(12) United States Patent
Mata Chavarria et al.

(10) Patent No.: US 9,631,172 B2
(45) Date of Patent: Apr. 25, 2017

(54) METHOD FOR MANUFACTURING A THREE-DIMENSIONAL BIOMIMETIC SCAFFOLD AND USES THEREOF

(71) Applicant: Queen Mary University Of London, London (GB)

(72) Inventors: Alvaro Mata Chavarria, Barcelona (ES); Juan Pablo Aguilar, Barcelona (ES)

(73) Assignee: Queen Mary University of London, London (GB)

( * ) Notice: Subject to any disclaimer, the term of this patent is extended or adjusted under 35 U.S.C. 154(b) by 188 days.

(21) Appl. No.: 14/386,804

(22) PCT Filed: Jan. 25, 2013

(86) PCT No.: PCT/EP2013/051465
§ 371 (c)(1),
(2) Date: Sep. 21, 2014

(87) PCT Pub. No.: WO2013/139508
PCT Pub. Date: Sep. 26, 2013

(65) Prior Publication Data
US 2015/0072429 A1    Mar. 12, 2015

(30) Foreign Application Priority Data
Mar. 21, 2012   (EP) ................................ 12382102

(51) Int. Cl.
*G01N 27/447*    (2006.01)
*C12N 5/00*     (2006.01)
(Continued)

(52) U.S. Cl.
CPC ............ *C12N 5/0068* (2013.01); *B03C 5/005* (2013.01); *C25D 13/00* (2013.01); *G01N 27/447* (2013.01); *G01N 27/453* (2013.01); *A61L 27/3633* (2013.01); *C12N 2533/30* (2013.01); *C12N 2533/50* (2013.01); *C12N 2533/76* (2013.01); *C12N 2535/10* (2013.01); *C12N 2537/00* (2013.01)

(58) Field of Classification Search
CPC ...... B03C 5/028; B03C 5/022; G01N 27/327; G01N 27/453; G01N 27/44756; G01N 27/44743; G01N 27/44713; A61L 27/36; A61L 27/3633
See application file for complete search history.

(56) References Cited

U.S. PATENT DOCUMENTS 8,906,684 B2 * 12/2014 Bhatia .................... C12P 21/00
435/325

OTHER PUBLICATIONS

Albrecht et al. (The Royal Society of Chemistry, vol. 7, pp. 702-709 (2007) (of record).*

(Continued)

*Primary Examiner* — Alexander Noguerola
(74) *Attorney, Agent, or Firm* — Stradley Ronon Stevens & Young LLP

(57) ABSTRACT

The present invention relates to a method for manufacturing a three-dimensional (3D) biomimetic scaffold that exploits the use of electrical fields and electrical insulating materials to pattern previously polymerized hydro gels with different molecules and/or macromolecular entities. The invention also relates to the 3D-biomimetic scaffolds obtained and to the uses and applications thereof.

9 Claims, 10 Drawing Sheets

(51) Int. Cl.
B03C 5/00 (2006.01)
G01N 27/453 (2006.01)
C25D 13/00 (2006.01)
A61L 27/36 (2006.01)

(56) References Cited

OTHER PUBLICATIONS

Dai X, et al., "Patterning nanoparticles in a three-dimensional matrix using an electric-field-assisted gel transferring technique", Langmuir, 2012, 28(5):2960-4.
Albrecht DR, et al., "Multiphase electropatterning of cells and biomaterials", Lab Chip, 2007, 7(6):702-9.
Khetan S and Burdick JA, "Patterning network structure to spatially control cellular remodeling and stem cell fate within 3-dimensional hydrogels", Biomaterials, 2010, 31(32):8228-34.
Nimmo CM and Shoichet MS, "Regenerative biomaterials that "click": simple, aqueous-based protocols for hydrogel synthesis, surface immobilization, and 3D patterning", Bioconjug Chem, 2001, 22(11):2199-209.
Deforest CA, et al., "Peptide-Functionalized Click Hydrogels with Independently Tunable Mechanics and Chemical Functionality for 3D Cell Culture", Chem. Mater., 2010, 22(16):4783-4790.

* cited by examiner

Fluorescent protein

1mm outside diameter
Tubes holded by a PDMS

Hydrogel
(Immobile phase)

Protein patterned in
agarose gel

METHOD FOR MANUFACTURING A THREE-DIMENSIONAL BIOMIMETIC SCAFFOLD AND USES THEREOF

FIELD OF THE INVENTION

The invention relates to the field of tissue engineering and regenerative medicine, and particularly to a method for manufacturing a three-dimensional (3D) biomimetic scaffold that exploits the use of electric fields and electrical insulating materials to pattern previously polymerized hydrogels with different molecules and/or macromolecular entities. The invention also relates to the 3D-biomimetic scaffolds obtained and to the uses and applications thereof.

BACKGROUND OF THE INVENTION

The microenvironment of a cell comprises all the cues (stimuli) affecting the cell and includes attachment to neighboring cells, attachment to the structural molecules of the extracellular matrix (e.g., via integrins), molecules secreted by the cell itself or by other cells, nutrients, oxygen, mechanical stimuli (such as shear stress), and many others. As well as requiring information from each other, cells derive a vast wealth of information from their environments, including the material that surrounds and separates them within tissues, the extracellular matrix (ECM).

Within the biomedical field, areas such as tissue engineering, regenerative medicine, drug discovery, or cell biology would highly benefit from the development of 3D biomimetic environments that recreate the complexity of the natural extracellular matrix. The general strategy is usually to seed cells within a scaffold, a structural device that defines the geometry of the replacement tissue and provides environmental cues that promote tissue regeneration. Yet for commercial success tissue engineering products must be not only efficacious but also cost-effective, introducing a potential dichotomy between the need for sophistication and ease of production.

Due to this necessity, the last twenty years have seen a rapid increase in the development of two-dimensional (2D) surface patterning techniques that allow to control with high precision and reproducibility the positioning and presentation of different molecules on surfaces. These studies have had a huge impact in areas like tissue engineering, biosensors, and cell and molecular biology studies in general.

There are many fabrication processes available to generate functional patterns of molecules on 2D surfaces. Examples include soft lithography techniques, dip pen nano lithography, photolithography, nanoimprint lithography, or microfluidic devices (Chen C. S. et al. 1997. Science, 276 (5317): 1425-1428; Chiche A. et al. 2008. Soft Matter, 4(14):2360-2364). Nonetheless, 2D patterns are a weak representation of the real cell environment and therefore there is great need to create structures or scaffolds that exhibit similar spatial control of bioactive molecules as those of 2D surfaces but within 3D. The extracellular matrix found in living tissues is a complex 3D highly hydrated environment made from many elements such as soluble or surface bound molecules, proteins, enzymes, and physical cues like pores and topographies. The precise spatial location of these molecules plays a key role in the behaviour of cells, tissues, and ultimately organs (Perez-Castillejos R. 2010. Materials Today, 13(1-2): 32-41).

The field of fabricating 3D hydrogels with patterns is much less developed and only recently have researchers begun to explore different approaches. Emerging techniques include: bioprinting multilayered structures (Moon S. J. et al. 2010. Tissue Engineering: Part C Methods. 16: 157-166; Fernandez J. G. and Khademhosseini A. 2010. Advanced Materials 22: 2538-2541; Aubin H. et al. 2010. Biomaterials 31: 6941-6951), additive photopatterning (Liu Tsang V. et al. 2007. FASEB Journal, 21: 790-801), stereolithography (Khetan S. et al. 2010. Methods in Bioengineering. Eds.: M. L. Yarmush and R. S. Langer. Artech House Publishing), microfluidics (Wong A. P. et al. 2008. Biomaterials 29: 1853-1861) and sequential click reactions with photoaddition (DeForest C. A. et al. 2010. Chemistry of Materials, 22: 4783-4790; Johnson L. M. et al. 2010. ACS Appl Mater Interfaces, 2(7): 1963-1972; DeForest C. A. et al. 2009. Nature Materials, 8: 659-664). However, none of these techniques uses an electric field to move the molecules that are going to pattern the 3D hydrogel.

Albrecht D. R. et al. (Albrecht D. R. et al. 2005. Lab Chip, 5(1): 111-118) disclosed a method for encapsulating live cells in 3D-hydrogels using dielectrophoresis. However, the dielectrophoretic forces to locate cells are applied over a prepolymer suspension and said prepolymer suspension is then polymerized by exposure to UV light. The same dielectrophoretic forces have been reported to be useful to locate microgels containing encapsulating bioactive materials such as proteins or cells (Albrecht D. R. et al. 2007. Lab Chip, 7: 702-709). Nevertheless, this method requires the use of special chambers with a plurality of micropatterned surface electrodes to design the position of the molecules or cells in the hydrogel.

Techniques such as bioprinting, additive photopatterning, stereolithography and microfluidics have the disadvantage that they do not allow fabricating scaffolds with inhomogeneous concentrations of soluble molecules. On the other hand, sequential click reactions and dielectrophoresis have the disadvantage that the material is exposed to UV radiation. Moreover, some of them are expensive and it is necessary sophisticated equipment and chemical reactions to get a controllable pattern.

Furthermore, some approaches have been published that use 3D synthetic hydrogels to support cell growth (Cushing M. C. and Anseth K. S. 2007. Science 316: 1133-1134). Nevertheless, in tissue engineering the selection of a 3D scaffold for culturing cells is dictated by the capability of producing that scaffold in large quantities and better strategies must be developed for delivering endogenous factors to the right place within the gel.

Although a great number of techniques for patterning molecules in 3D hydrogels are known, there are some drawbacks which are still unsolved and limit their applications.

It is therefore necessary to develop further techniques for patterning molecules in 3D hydrogels to allow building more mimetic cell environments and which are capable of solving all or some of the above mentioned drawbacks related to the techniques of the state of the art.

SUMMARY OF THE INVENTION

It has been now surprisingly found that using a lithographic technique that exploits dielectrophoretic forces to pattern previously polymerized hydrogel materials with different charged molecules in three-dimensions allows the formation of 3D biomimetic scaffolds having inhomogeneous concentrations of soluble molecules and avoiding the exposition of the material to UV radiation. The method of the invention allows the generation of precise and reproducible well organized patterns of molecules within a wide range of hydrogel materials by modulating the electric field by the use of an electrical insulating material. Sections 2.1 and 2.2 of the Examples show the results obtained with the method of the invention when the electric field is not significantly affected and when the electric field is affected by a porous membrane of polydimethylsiloxane, respectively.

A great advantage of this technique is its versatility: since the technique relies on the application of an electric field, any type of charged molecule can be patterned within any type of hydrogel. This method is simple, easy to handle and affordable and does not need complex equipment. A chamber having only two electrodes as used for protein electrophoresis is enough. It serves as a micro/nano fabrication lithographic technique with potential use in any soft-matter material.

The authors have surprisingly found that the resulting 3D biomimetic scaffolds obtained support cell growth. Section 2.3 of the Examples show that mesenchymal cells cultured on the top of a slice of the 3D biomimetic scaffold obtained according to the method of the invention are capable of attaching to the adhesive peptides patterned on the scaffold and to spread on the region where said peptides are patterned.

The resulting 3D biomimetic scaffolds show an extremely high level of bioactivity and anisotropy and are suitable for applications in tissue engineering, regenerative medicine, in vivo-like models for drug screening, or cell biology studies such as embryogenesis, spinal cord regeneration or cancer metastasis.

Therefore, it is an objective of the present invention, the production and uses of 3D biomimetic scaffolds based on the use of dielectrophoretic forces to pattern previously polymerized hydrogels.

Thus, in an aspect, the invention relates to a method for manufacturing a three-dimensional (3D) biomimetic scaffold comprising:
  a) contacting a mobile phase with an immobile phase through an electrical insulating material containing the mobile phase, said electrical insulating material selected from the group consisting of:
    (i) a porous membrane placed on the surface of the top of the immobile phase, said porous membrane defining the geometrical regions through which the mobile phase passes;
    (ii) at least a tube inserted into the top of the immobile phase; and
    (iii) a combination of (i) and (ii);
  b) subjecting said mobile phase and said immobile phase in the presence of the electrical insulating material to a direct current (DC) electric field created inside a chamber and applied in closed circuit by a pair of electrodes in vertical or horizontal configuration, said chamber containing the mobile phase, the immobile phase and the electrical insulating material covered by a buffer; and
  c) patterning the immobile phase with the components of the mobile phase, in which said components move by forming patterns within the immobile phase and are not separated by their molecular weight and in which the location of the components of the mobile phase is controlled as desired by modulating the electric field and the time;
  wherein the mobile phase is an aqueous or organic medium comprising at least a charged compound and/or a charged macromolecular entity; and
  wherein the immobile phase is any previously polymerized hydrogel.

In another aspect, the invention relates to a three-dimensional (3D) biomimetic scaffold obtainable by the method according to the invention or a fragment thereof.

In another aspect, the invention relates to a three-dimensional (3D) biomimetic scaffold according to the invention or to a three-dimensional (3D) biomimetic scaffold obtained according to the method of the invention or a fragment thereof for use in medicine.

In another aspect, the invention relates to a three-dimensional (3D) biomimetic scaffold according to the invention or to a three-dimensional (3D) biomimetic scaffold obtained according to the method of the invention or a fragment thereof for use in the replacement, reparation or regeneration of a damaged, dysfunctional or pathological tissue.

In another aspect, the invention relates to the use of a three-dimensional (3D) biomimetic scaffold according to the invention or to a three-dimensional (3D) biomimetic scaffold obtained according to the method of the invention or a fragment thereof as an in vivo-like model for drug screening or as a model for molecular or cell biology studies.

In another aspect, the invention relates to the use of a three-dimensional (3D) biomimetic scaffold according to the invention or to a three-dimensional (3D) biomimetic scaffold obtained according to the method of the invention or a fragment thereof to support cell growth.

DETAILED DESCRIPTION OF THE INVENTION

Figure 1:
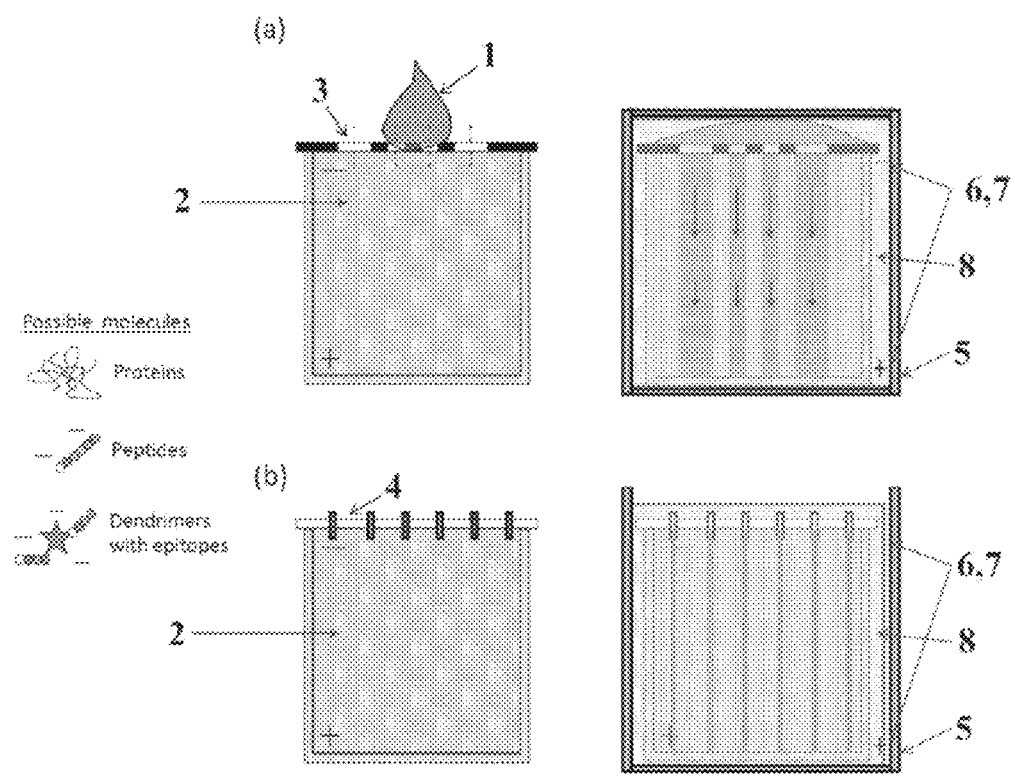
FIGS. 1A and 1B. Components of the method of the invention for manufacturing 3D biomimetic scaffolds. (A) Using a porous membrane (3) as electrical insulating material. Left: Mobile phase (1) comprising a solution of molecules passing through a porous membrane (3) in order to pattern an immobile phase (2). Right: Device submerged in buffer (8) inside a chamber (5) having two electrodes (6) and (7) and patterns formed according to the method of the invention. Arrows indicate the direction in which the mobile phase (1) runs. (B) Using tubes (4) filled with proteins as electrical insulating material. Left: Tubes (4) filled with mobile phase (1) in order to pattern an immobile phase (2). Right: Device submerged in buffer (8) inside a chamber (5) having two electrodes (6) and (7) and patterns formed according to the method of the invention.

The present invention provides 3D biomimetic scaffolds, methods for producing said scaffolds, and applications thereof.

Method for Manufacturing 3D Biomimetic Scaffolds

In an aspect, the invention relates to a method, hereinafter referred to as the "method of the invention", for manufacturing a three-dimensional (3D) biomimetic scaffold comprising:
  a) contacting a mobile phase with an immobile phase through an electrical insulating material containing the mobile phase, said electrical insulating material selected from the group consisting of:
    (i) a porous membrane placed on the surface of the top of the immobile phase, said porous membrane defining the geometrical regions through which the mobile phase passes;
    (ii) at least a tube inserted into the top of the immobile phase; and
    (iii) a combination of (i) and (ii);
  b) subjecting said mobile phase and said immobile phase in the presence of the electrical insulating material to a direct current (DC) electric field created inside a chamber and applied in closed circuit by a pair of electrodes in vertical or horizontal configuration, said chamber containing the mobile phase, the immobile phase and the electrical insulating material covered by a buffer; and
  c) patterning the immobile phase with the components of the mobile phase, in which said components move by forming patterns within the immobile phase and are not separated by their molecular weight and in which the location of the components of the mobile phase is controlled as desired by modulating the electric field and the time;
wherein the mobile phase is an aqueous or organic medium comprising at least a charged compound and/or a charged macromolecular entity; and
wherein the immobile phase is any previously polymerized hydrogel.

The "method of the invention" is a lithographic technique that exploits electrical fields (dielectrophoresis) to pattern previously polymerized hydrogel materials with different charged compounds and/or macromolecular entities in three dimensions.

The expression "lithographic technique", as used herein, refers to a method for creating micropatterns of bioactive molecules and/or macromolecular entities in a hydrogel material.

The method of the invention allows manufacturing 3D biomimetic scaffolds. The expression "3D biomimetic scaffold", as used in the present invention, refers to a three-dimensional artificial structure that partially or completely mimics (e.g. replicates, reproduces, imitates or is similar to) the natural extracellular matrix in its structure or function and exhibits a precise spatial location of bioactive molecules and/or macromolecular entities.

The extracellular matrix (ECM) is the extracellular part of animal tissue that usually provides structural support to the animal cells in addition to performing various other important functions such as segregating tissues from one another and regulating intercellular communication. In addition, it sequesters a wide range of cellular growth factors and acts as a local depot for them. The extracellular matrix is composed of proteins and polysaccharides that cells secrete into their environment. The nature, form and composition of the ECM is diverse and it depends on the types of cells it is associated with. Thus, the 3D biomimetic scaffold of the invention is capable of recreating the complexity of the natural extracellular matrix found in living tissues. The types of scaffolds manufactured will depend on the specific design and application.

The term "three-dimensional" or "3D", as used herein, means that the biomimetic scaffold of the invention has three dimensions, i.e. that three co-ordinates are needed to locate a molecule within it. The three-dimensional shape of the biomimetic scaffold may be any 3D shape, size, configuration, depth, width, or other geometry capable of being formed in a mold, and further capable of being reproduced by downstream steps (i.e. capable of being adopted by a polymerizable compound). In one embodiment the 3D shape formed is similar to or representative of a 3D geometry found in a biological system.

The responsible of the 3D shape of the biomimetic scaffold is the immobile phase of the method of the invention.

The term "immobile phase", as used herein, refers to any previously polymerized hydrogel that is going to be patterned with the mobile phase. The term "hydrogel" refers to water-insoluble three-dimensional networks that are formed by the cross-linking of water-soluble monomers. The cross-linking of the water soluble monomers into a water insoluble polymer allows the hydrogel to "swell" and topologically trap other compounds or macromolecular structures, thereby forming an interpenetrating covalent network in and around the molecules trapped. Any hydrogel may be used in the present invention.

For the present purposes, the hydrogels used in the method of the invention are previously polymerized hydrogels. By "previously polymerized" it is meant that the cross-linking of water-soluble monomers has been reached before starting to apply the method of the invention and that the immobile phase of the method of the invention is a network of interacting polymer chains that are highly hydrated, having a elasticity similar to that of natural tissues. The previously polymerized hydrogel may contain cells entrapped or encapsulated within the hydrogel during the polymerization step. Thus, in a preferred embodiment, at least a cell is contained in the previously polymerized hydrogel used in the method of the invention before starting to apply an electric field. In another embodiment a fragment of a cell is contained in the previously polymerized hydrogel. In yet another embodiment, at least a compound selected from a peptide, a protein, a nucleic acid, a nanoparticle, a microparticle, a dendrimer, a dendrimer conjugate or a drug is contained in the previously polymerized hydrogel.

The process of the invention allows the generation of precise patterns of molecules within a wide range of hydrogel materials, including traditional ones like agarose and polyacrylamide or cutting edge ones like those formed through self-assembling materials. Some known natural polymers and synthetic monomers used in hydrogel fabrication include, without limitation, chitosan, alginate, fibrin, fibronectin, collagen, gelatin, elastin, hyaluronic acid, heparan sulfate, chondroitin sulfate, keratan sulfate, dextran, hydroxyethyl methacrylate, N-(2-hydroxypropyl) methacrylate, N-vinyl-2-pyrrolidone, N-isopropyl acrylamide, vinyl acetate, acrylic acid, methacrylic acid, polyethylene glycol diacrylate/methacrylate, polyethylene glycol diacrylate/dimethylacrylate, polyacrylamide, agarose, just to name a few.

In an embodiment the hydrogel useful in the present invention is selected from polyacrylamide, agarose, chitosan, alginate, gelatin and the commercially available BD™ PuraMatrix™ Peptide Hydrogel (BD Biosciences). Preferred hydrogels are polyacrylamide hydrogel and agarose hydrogel, more preferably agarose hydrogel. The concentrations of the monomers in the hydrogel depend on the specific hydrogel used. Typical concentrations of the monomers in the hydrogel are between 4% and 16% for polyacrylamide, preferably 8%; between 1% and 5% for agarose, preferably 2%; between 0.5% and 2% for chitosan, preferably 1.5%; between 1% and 3% for alginate, preferably 2%; and between 5% and 10% for gelatin, preferably 5%. These concentrations permit the pattern conformation.

When the 3D biomimetic scaffold of the invention is going to support cell growth, agarose hydrogel is preferred.

In a preferred embodiment the hydrogel is agarose. Typical concentration of agarose in the hydrogel may be from 0.5 to 5, preferably 2%. These concentrations permit the conformation of patterns. It is possible to use a higher concentration of agarose, although it compromises the handelability due to the viscosity of the agarose melt solution.

The hydrogel may also be a bioactive hydrogel with sites designed to bind passing molecules.

The polymerized hydrogels may be prepared in situ by different methods well known by the skilled person depending on the monomer used or may be commercially available.

In general, the monomer to be polymerized is mixed with the same buffer used in the method for covering the mobile phase, the immobile phase and the electrical insulating material in step (b) of the method of the invention. This mixture forms a pre-gel solution. Then, the pre-gel solution of this polymerizable material is poured into a mold and may be manufactured by a method such as that described in section 1.1.2 of the Examples. When the electrical insulating material is going to be a porous membrane, a piece of the polymer used for manufacturing the membrane or a mold having the same shape than the membrane without holes is placed on top of the immobile phase to get the space where the membrane will be located. After the hydrogel is polymerized, said piece or mold is substituted by the porous membrane that is going to be used in the method of the invention. When the electrical insulating material is going to be a combination of a porous membrane and one or more tubes, or a tube or a series of tubes without the membrane, the single tube or a series of plugged tubes of plastic or crystal are inserted through the polymer used for manufacturing the membrane. The ensemble of the polymer for manufacturing the porous membrane and the tube or tubes are positioned on the top of the liquid before the pre-gel polymerizes into hydrogel. After the hydrogel is polymerized, when the electrical insulating material includes the membrane, the plugged tubes are substituted by hollow tubes filled with mobile phase. On the other hand, when only the tubes are used, the membrane is removed and the holes made by the plugged tubes are filled by hollow tubes containing the mobile phase. The porous membrane is obtained by curing the polymer inside the mold in which the hydrogel polymerizes. In this context, "curing" is a term in polymer chemistry that refers to the toughening or hardening of a polymer material by cross-linking of polymer chains. Once this is prepared, the hydrogel is allowed to polymerize.

The polymerization is achieved through the use of temperature, time, a polymerizing agent, and/or any other polymerization trigger. The polymerization requirements will depend upon the particular polymerizable monomer or the polymerizing compound chosen.

For certain applications, for example when the mobile phase contains cells, hydrogels of high porosity are needed. Porous hydrogels suitable for the present invention may be obtained by freeze drying (Madihally S. V. and Matthew H. W. 1999. Biomaterials, 20(12): 1133-42) or by using dense gas $CO_2$ as a foaming agent (Ji C. et al. 2011. Acta Biomater, 7(4): 1653-64).

The mold defines the shape of the immobile phase which will be the shape of the 3D biomimetic scaffold obtained by the method of the invention. The shape of the biomimetic scaffold may be any desired shape. Possible shapes are, without limitation, cylindrical, cubic, cuboidal, any kind of prism shape (triangular, rectangular, pentagonal, hexagonal, etc.). In general, the mold in which the hydrogel polymerizes is the same mold that is going to be subjected to an electric field in step b) of the invention. Thus, the mold may be of any material capable of accepting a three-dimensional shape while being sufficiently rigid to maintain the shape in downstream steps of the method. The mold may be manufactured in one piece or may be formed by different pieces to be assembled to prepare the hydrogel. Preferred materials for the mold are PDMS, crystal, thermoplastic, and other materials that allow manufacturing any desired shape or form.

In a particular embodiment, the mold is a typical mold for protein electrophoresis.

Typical vertical slab hydrogels are normally cast between a pair of glass plates for support. A space is constructed by separating the two plates with spacer strips down the edges of the plates, then sealing the edges and bottom to form a liquidtight box or sandwich. The hydrogels for the method of the invention may be of any desired size. Typical hydrogels for this invention range in size from 2 to 21 cm×3 to 30 cm and from 0.2 to 7 cm thick; preferably 8.3 cm×9.7 cm and from 0.2 to 0.5 cm thick.

A gasket or form comprising the bottom of the molding cavity is removed after hydrogel polymerization in order to allow current to pass through two opposite edges of the hydrogel slab; one of these edges represents the open (top) surface of the hydrogel cavity, and the other is formed against its removable bottom.

As used herein, the term "mobile phase" refers to the phase that is displaced through the hydrogel when performing the method of the invention and that contains the bioactive molecules and/or macromolecular entities that are going to pattern the hydrogel. The mobile phase is an aqueous or organic medium comprising at least a charged compound and/or a charged macromolecular entity.

The expression "aqueous or organic medium" refers to a solution that contains the compound(s) and/or macromolecular entity and provides the mobile phase with the right density for running the molecules. As used herein, the term "aqueous medium" refers to a liquid medium composed largely, but not necessarily exclusively, of water; preferably comprising at least 50 weight percent water. Other components may also be present, such as salts, co-solvents, buffers, colorants and the like. In a preferred embodiment the medium is an aqueous medium. In an embodiment the aqueous medium is 2% low melting agarose in the same buffer used for step (b) of the method of the invention. In another embodiment the aqueous medium is glycerol in the same buffer used for step (b) of the method of the invention. As used herein, the term "organic medium" refers to a liquid medium composed largely, but not necessarily exclusively, of one or more organic solvents, it being possible for said medium to contain water; preferably comprising at least 50 weight percent organic solvents. Examples of organic solvents for organic medium that may be used in the invention are, without limitation, dimethyl sulfoxide (DMSO), dimethylformamide (DMF), ethanol, methanol, dichloromethane (DCM), $CHCl_3$, hexane, pentane, heptane, bencene, toluene and acetone.

Since the method of the invention relies on the application of an electrical field, any type of hydrogel can be patterned using any charged molecule. The term "charged" refers to the electric charge that the compound or macromolecular entity has at the pH at which step (b) of the method of the invention is performed.

Because the only requirement for a molecule to be moved and positioned within the hydrogel is to be charged, many types of proteins, enzymes, peptides or other molecular structures can be used.

The goal of the 3D biomimetic scaffold of the invention is to mimic the natural extracellular matrix. Thus, the mobile phase contains the components usually present in the ECM. Components of the ECM are produced intracellularly by resident cells, and secreted into the ECM via exocytosis. Once secreted, they then aggregate with the existing matrix.

The term "compound" as used herein referred to the mobile phase, relates to any kind of charged molecule capable of being displaced through a hydrogel when an electric field is applied and includes bioactive molecules and structural molecules, soluble and surface bound molecules. Compounds useful in the present invention are, without limitation, peptides, proteins, nucleic acids, nanoparticles, microparticles, fluorescent molecules, dendrimers, dendrimers conjugated with epitopes or drugs or fluorescent molecules, hormones, growth factors, enzymes, drugs, etc.

In a preferred embodiment the compound is selected from a peptide, a protein, a nucleic acid, a nanoparticle, a microparticle, a dendrimer or a peptide-dendrimer conjugate; preferably is selected from a peptide, a protein, a dendrimer and a peptide-dendrimer conjugate.

The term "peptide" or "polypeptide", as used herein, refers to a short polymer of amino acid monomers linked by peptide bonds, typically containing less than 50 monomer units. Any peptide may be used in the present invention. In a preferred embodiment the compound is a peptide.

The term "protein", as used herein, refers to one or more peptides (or polypeptides), i.e., polymer chains of amino acids bonded together by peptide bonds between the carboxyl and amino groups of adjacent amino acid residues, optionally including modifications, e.g., post-translational modifications, which alter the physical and chemical properties, folding, stability, activity, and ultimately, the function of the proteins. Proteins having non-peptide groups attached (i.e., prosthetic groups or cofactors) are also included within this definition. The number of amino acid residues in a protein can vary in a broad range, for example, the polymer chain of amino acid residues linked by peptide bonds may contain typically 50 or more amino acids residues. Examples of proteins useful in the present invention are, without limitation, perlecan, agrin, collagen XVIII. In a preferred embodiment the compound is a protein. In a more preferred embodiment the compound is an elastin-like polymer or a mixture thereof. Elastin-like polymers consist of repeating pentapeptide domains of the amino acids VPGIG and VPGKG or VPGVG with the cell binding sequence RGDS.

The term "nucleic acid", as used herein, refers to a polymer of nucleotides having two or more deoxyribonucleotide, ribonucleotide or nucleotide analog molecules as well as molecules that are structurally similar to a native nucleic acid, but differ from the native nucleic acid (e.g. through chemical modification) at one or more of the nucleic acid backbone (e.g. phosphate in native nucleic acids), nucleic acid sugar (e.g. deoxyribose for native DNA and ribose in native RNA), and nucleic acid base (e.g. adenosine, cytosine, guanine or thymidine in native nucleic acids). The nucleic acid can be a double stranded or single stranded nucleic acid including, without limitation, DNA, RNA, oligonucleotides, PNAs, cDNA, RNAi, shRNA, miRNA, siRNA, ribozymes, antisense oligonucleotides, as well as modified forms thereof. In a preferred embodiment the compound is a nucleic acid.

The term "nanoparticle", as used herein, refers to a particle having a diameter below 1 µm and including, without limitation, nanospheres and nanocapsules. In a preferred embodiment the compound is a nanoparticle.

The term "microparticle", as used herein, refers to a particle having a diameter between 1 and 250 µm and including, without limitation, microspheres and microcapsules. In a preferred embodiment the compound is a microparticle.

The term "dendrimer", as used herein, refers to a repetitively branched molecule typically symmetric around the core, and often adopting a spherical three-dimensional morphology. The person skilled in the art knows that any type of dendrimer may be used. In a preferred embodiment the compound is a dendrimer. In a more preferred embodiment the compound is a peptide-dendrimer conjugate. The term "peptide-dendrimer conjugate" refers to a dendrimer conjugated to one or more epitopes to homogenize the size and the charge of said peptides.

The compound may be a molecule capable of exerting a function, preferably a biological function. In a preferred embodiment the compound is selected from a hormone, a growth factor, an enzyme, a fluorescent molecule, a drug, a fluorescent molecule-dendrimer conjugate or a drug-dendrimer conjugate.

The term "hormone", as used herein, refers to a chemical released by a cell or a gland in one part of the body that sends out messages that affect cells in other parts of the organism. Examples of hormones that are useful in the present invention are, without limitation, melatonin (MT), serotonin (5-HT), thyroxine (T4), triiodothyronine (T3), epinephrine or adrenaline (EPI), norepinephrine or noradrenaline (NRE), dopamine (DPM or DA), antimullerian hormone or mullerian inhibiting hormone (AMH), adiponectin (Acrp30), adrenocorticotropic hormone or corticotrophin (ACTH), angiotensinogen and angiotensin (AGT), antidiuretic hormone or vasopressin (ADH), atrial natriuretic peptide or atriopeptin (ANP), calcitonin (CT), cholecystokinin (CCK), corticotrophin-releasing hormone (CRH), erythropoietin (EPO), follicle-stimulating hormone (FSH), gastrin (GRP), ghrelin, glucagon (GCG), gonadotrophin-releasing hormone (GnRH), growth hormone-releasing hormone (GHRH), human chorionic gonadotrophin (hCG), human placental lactogen (HPL), growth hormone (GH or hGH), inhibin, insulin (INS), insulin-like growth factor or somatomedin (IGF), leptin (LEP), luteinizing hormone (LH), melanocyte stimulating hormone (MSH or α-MSH), orexin, oxytocin (OXT), parathyroid hormone (PTH), prolactin (PRL), relaxin (RLN), secretin (SCT), somatostatin (SRIF), thrombopoietin (TPO), thyroid-stimulating hormone or thyrotropin (TSH), thyrotropin-releasing hormone (TRH), cortisol, aldosterone, testosterone, dehydroepiandrosterone (DHEA), androstenedione, dihydrotestosterone (DHT), estrone, estriol (E3), progesterone, calcitriol, calcidiol, prostaglandins (PG), leukotrienes (LT), prostacyclin (PGI2), thromboxane (TXA2), prolactin releasing hormone (PRH), lipotropin (PRH), brain natriuretic peptide (BNP), neuropeptide Y (NPY), histamine, endothelin, pancreatic polypeptide, renin and enkephalin. In a preferred embodiment the compound is a hormone.

The term "growth factor", as used herein, refers to a naturally occurring substance capable of stimulating cellular growth, proliferation and cellular differentiation. Usually it is a protein or a steroid hormone. Growth factors typically act as signalling molecules between cells. Examples of growth factors are cytokines that bind to specific receptors on the surface of their target cells. Their function varies between growth factors. For example, bone morphogenic proteins stimulate bone cell differentiation, while fibroblast growth factors and vascular endothelial growth factors stimulate blood vessel differentiation (angiogenesis). Examples of growth factors are, without limitation, adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factors (FGFs), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), migration-stimulating factor, myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), tumor necrosis factor alpha (TNF-α), vascular endotelial growth factors (VEGFs), placental growth factor (PlGF), IL-1, IL-2, IL-3, IL-4, IL-5, IL-6 and IL-7. In a preferred embodiment the compound is a growth factor.

The term "enzyme", as used herein, refers to a protein that catalyzes chemical reactions. Examples of enzymes useful in the present invention are, without limitation, serine proteases, threonine proteases and matrix metalloproteinases. In a preferred embodiment the compound is an enzyme.

The term "fluorescent molecule", as used herein, refers to a molecule capable of emitting fluorescence. Any fluorescent molecule may be used in the present invention. Examples of fluorescent molecules are, without limitation, pyrene, fluorescein and luciferin. In a preferred embodiment the compound is a fluorescent molecule. In a more preferred embodiment the compound is a fluorescent molecule-dendrimer conjugate, i.e. a dendrimer conjugated to one or more molecules that emit fluorescence.

The term "drug", as used herein, relates to any chemical substance that, when absorbed into the body of a living organism, alters normal bodily function or that is used in the treatment, cure, prevention or diagnosis of a disease or enhances physical or mental well-being. Examples of drugs useful in this invention are, without limitation, cancer drugs such as isotretinoin, tretinoin, cladribine, azacitidine, fluorouracil, mercaptopurine, thioguanine, paclitaxel, actinomycin-D, doxorubicin, daunorubicin, everolimus, anagrelide, aldesleukin, alemtuzumab, pemetrexed, alitretinoin, vinblastine, melphalan, interferon alfa, altretamine, methotrexate, amifostine, aminoglutethimide, anastrozole, exemestane, nelarabine, bleomycin, busulfan, capecitabine, carboplatin, carmustine, chlorambucil, cisplatin, cyclophosphamide, ifosfamide, carmustine, cytarabine, dacarbazine, docetaxel, vincristin, vinblastine, leucovorin, irinotecan, idarubicin, mitomycin C, oxaliplatin, raltitrexed, tamoxifen, carboplatin, mitoxantrone, blenoxane, mithramycin, 2-methoxyestradiol, prinomastat, batimastat, BAY 12-9566 and temozolamide; osteoporotic drugs such as risedronate, ibandronate, conjugated estrogens, estradiol, raloxifene, teriparatide, calcitonin, alendronate, hydrochlorotiazide, medroxyprogesterone, denosumab, zoledronic acid and estradiol; arthritis drugs such as hydroxychloroquine, chloroquine, leflunomide, methotrexate, sulfasalazine, azathioprine, cyclophosphamide, cyclosporine, minocycline, penicillamine, abatacept, adalimumab, anakinra, etanercept, infliximab, rituximab, tocilizumab, aspirin, ibuprofen, naproxen, prednisone, acetaminophen and tramadol. Other drugs suitable are described in detail in The Merck Index in CD-ROM, 13rd Edition. In a preferred embodiment the compound is a drug. In a more preferred embodiment the compound is a drug-dendrimer conjugate. The term "drug-dendrimer conjugate" refers to a conjugate of a dendrimer with one or more drugs wherein the dendrimer acts as a carrier for said drugs and is used for drug delivery.

As used herein, the term "macromolecular entity" refers to a charged structure formed by more than one molecule and includes cells and fragments thereof as well as bacteria.

Any cell may be used in the present invention. Suitable cells for the invention are cell types involved in ECM formation such as fibroblasts, chondrocytes and osteoblasts. Other kind of cells useful are, without limitation, stem cells, mesenchymal stem cells, melanoma cell lines such as COLO-794, COLO-800, COLO-818, FM-28, WM-75, WM-793, WM-852, FR-M-170, FR-M-204, Ma-Mel-16, Ma-Mel-25, and other melanoma cell lines listed in the European Searchable Tumour Line Database (ESTDAB) (http://www.ebi.ac.uk/ipd/estdab/). In a preferred embodiment the macromolecular entity is a cell. Fragments of cells included in the present invention may be cell membranes. By "cell membrane" it is understood a biological membrane that separates the interior of a cell from the outside environment. It consists of the lipid bilayer with embedded proteins. In another preferred embodiment the macromolecular entity is a fragment of a cell, preferably a cell membrane.

In another preferred embodiment the macromolecular entity is a bacterium. Any bacteria may be used in the present invention. Examples of bacteria are, without limitation, *Escherichia coli, Shigella* spp., *Bacillus cereus, Yersinia pestis, Pseudomonas* spp., *Bordetella pertussis, Borrelia burgdorferi, Campylobacter pylori, Chlamydia trachomatis, Clostridium botulinum, Clostridium difficile, Clostridium perfringens, Clostridium tetani, Corynebacterium diphtheriae, Enterococcus faecalis, Haemophilus influenzae, Helicobacter pylori, Klebsiella pneumoniae, Lactobacillus acidophilus, Legionella pneumophila, Listeria monocytogenes, Mycobacterium diphtheriae, Mycobacterium tuberculosis, Mycoplasma pneumoniae, Neisseria gonorrhoeae, Neisseria meningitidis, Salmonella* spp., *Shigella dysenteriae, Staphylococcus aureus, Streptococcus* spp. and *Vibrio cholerae*.

The mobile phase is prepared by dissolving or suspending the compounds or the macromolecular entities in the aqueous or organic solution by methods well known in the art.

Step a) of the method of the invention involves contacting the mobile phase with the immobile phase through an electrical insulating material containing the mobile phase.

The term "electrical insulating material", as used herein, refers to a material that has a relative static permittivity or dielectric constant greater than 1. The expression "relative permittivity" refers to the extent to which a material concentrates electrostatic lines of flux. The relative permittivity is the ratio of the amount of electrical energy stored in a material by an applied voltage, relative to that stored in a vacuum. And it is static when it is calculated in a frequency of zero. The relative static permittivity or dielectric constant for an electrical insulating material may be calculated for methods well known by the person skilled in the art. Specifically, the capacitance of a test capacitor, $C_0$, is measured with vacuum between its plates. Then, using the same capacitor and distance between its plates, the capacitance $C_x$ with a dielectric between the plates is measured. The relative dielectric constant can be then calculated as $\in_r = C_x/C_0$.

Therefore, the electric insulating material modifies the electric field applied in step (b) of the method of the invention. Said electrical insulating material is also named "mobile container" in the Examples of the present description, since it contains the mobile phase and guides the patterning of the molecules within the hydrogel. Examples of electrical insulating materials are glass, paper, teflon, rubber-like polymers and most plastics.

The electrical insulating material useful in this invention is selected from:

(i) a porous membrane placed on the surface of the top of the immobile phase, said porous membrane defining the geometrical regions through which the mobile phase passes;
(ii) at least a tube inserted into the top of the immobile phase; and
(iii) a combination of (i) and (ii).

The dimension and position of the electrical insulating material is one of the factors involved in controlling the location of the components of the mobile phase through the immobile phase.

The term "porous membrane", as used herein, refers to a layer of electrical insulating material that has one or more holes that allow the mobile phase pass through said membrane. The term "porous" does not refer to the porosity of the insulating material. The membrane is "porous" because it has one or more holes through which the mobile phase passes and said holes are the "pores" of the membrane. Said holes or "pores" define the geometrical regions through which the mobile phase passes and may be open-holes or may be filled with tubes that contain the mobile phase. By "geometrical regions" it is understood the x-y shape through which the molecules will pass. The geometry of said holes depends on the particular pattern to be obtained in the hydrogel. Each hole may be a rectangular hole, a cylindrical hole, or any other shape. Each hole may be filed with a different mobile phase. The porous membrane as such can be easily modulated to exhibit almost any design. The shape of the membrane may be any desired shape. In a preferred embodiment the porous membrane is rectangular. The porous membrane can be of various thickness, particularly preferred are from 200 μm to 0.5 cm, more preferably 0.3 cm. The porous membrane must be made from an electrical insulating material. Materials suitable for said porous membrane are, without limitation, polyurethane, polycarbonates, ethylene-vinyl acetate, silicone rubber such as polydimethylsiloxane, fluorosilicone rubber, polyacrylic rubber, chlorosulfonated polyethylene, ethylene propylene rubber and chloroprene; preferably polydimethylsiloxane (PDMS). A method for preparing said porous membrane is disclosed in the Examples. A cylindrical horizontal container for the mobile phase is made in the membrane by the use of a tube in horizontal position. Then, the geometrical regions through which the mobile phase passes are made by inserting tubes in the membrane or by making holes with sharp razors, soft lithography or other suitable technique well known in the art. The porous membrane is placed on the surface of the top of the immobile phase, i.e. in contact with the upper edge of the hydrogel. In an embodiment the geometrical regions of the porous membrane are defined by holes in said membrane. In another embodiment the geometrical regions of the porous membrane are defined by tubes inserted in the holes of said membrane. The use of a porous membrane as electrical insulating material creates a modification of the electrical field (see section 2.2 of the Examples).

The use of this membrane may not be necessary for less complex designs. Alternatively, small tubes containing the mobile phase may be sufficient to define the areas where the compounds or macromolecular entities will be patterned. Said small tubes are placed in the locations where the mobile phase will be applied.

The term "tube", as used herein and referred to the electrical insulating material of the invention, is a rigid and hollow cylinder, usually but not necessarily of circular cross-section, used to convey the mobile phase. In fact, tubes suitable for the present invention may be tubes having triangular, square, rectangular, pentagonal, hexagonal or any other cross-section. Said tubes can have a different length depending on the hydrogel size. Preferred length is from 0.5 cm to 10 cm, more preferably of 3.5 cm. Suitable electrical insulating materials for tubes are, without limitation, silica, quartz, crystal, plastic; preferably crystal or plastic. The tube must be inserted into the top of the immobile phase, i.e. inserted into the upper edge of the hydrogel. When only tubes are used as electrical insulating materials, these tubes do not create a significant modification of the electrical field (see section 2.1 of the Examples).

In another embodiment the electrical insulating material is a combination of a porous membrane and at least a tube.

The electrical insulating material contains the mobile phase. This means that the holes of the porous membrane or the tubes are filled with the mobile phase.

Thus, the first step of the method of the invention [step (a)] implies filling the holes of the porous membrane or the tubes with the mobile phase. This must be done by means known by the person skilled in the art just before to start step (b) of the method of the invention.

Step (b) of the method of the invention consists of subjecting the ensemble formed by the mobile phase, the immobile phase and the electrical insulating material to a direct current (DC) electric field created inside a chamber and applied in closed circuit by a pair of electrodes in vertical or horizontal configuration, wherein the chamber contains the mobile phase, the immobile phase and the electrical insulating material covered by a buffer. Therefore, step (b) of the method of the invention is based on the dielectrophoretic principle.

The ensemble formed by the mobile phase, the immobile phase and the electrical insulating material must be inside a chamber. The term "chamber" means a typical electrophoretic chamber or a chamber specially designed for the manufacturing of the biomimetic scaffold of the invention that has essentially the same features that a typical electrophoretic chamber. Said chamber is designed to perform the migration of the mobile phase by applying an electric field. These chambers typically consist of a nonconducting material (e.g., glass, acrylic) and include a pair of electrodes.

The term "electrode", as used herein, relates to an electrical conductor used to make contact with a nonmetallic part of a circuit, in this case with an electrolyte. By "pair of electrodes" it is meant that the chamber has only two electrodes: an anode and a cathode. The anode is the positive (+) electrode and the cathode is the negative (−). The electrons enter the device through the cathode and exit the device through the anode. Materials for electrodes may be, without limitation, platinum wire, silver and gold.

A hydrogel is typically mounted on a suitable electrophoresis apparatus, so that one edge of the hydrogel contacts a first buffer reservoir containing an electrode and the opposite hydrogel edge contacts a second reservoir with a second electrode, steps being taken so that the current passing between the electrodes is confined to run mainly or exclusively through the hydrogel.

The method of the invention may be performed in vertical configuration or in horizontal configuration, preferably in vertical configuration.

The expression "vertical configuration", as used herein, means that the hydrogel's upper edge is in contact with an upper buffer reservoir and the lower edge is in contact with a lower reservoir. Vertical electrophoresis has an angle 90 degree to the bottom side. Thus, the mobile phase runs through the immobile phase in a vertical direction.

The expression "horizontal configuration", as used herein, means that the hydrogel is run in a horizontal orientation with the gel resting on a platform between the buffer reservoirs, submerged under a layer of a few millimeters of buffer. Horizontal electrophoresis has an angle 180 degree to the bottom side. Thus, the mobile phase runs through the immobile phase in a horizontal direction.

The chamber contains the mobile phase, the immobile phase and the electrical insulating material covered by a buffer. The tube(s) or porous membrane used as electrical insulating material must be completely submerged in buffer. In this context, the term "buffer" relates to the buffer solution used for running the electrophoresis. Said "buffer" is an aqueous solution consisting of a mixture of a weak acid and its conjugate base or a weak base and its conjugate acid. It has the property that the pH of the solution changes very little when a small amount of strong acid or base is added to it. Preferred pH for the buffer of the invention is 7.4, which is the normal extracellular pH. However, the 3D biomimetic scaffold of the invention may be used as a model for diseases in which physiological pH is altered. Thus, buffer solutions useful in this invention are, without limitation, tris-HCl (range of pH 7.5 to 9.0), tris-glycine (range of pH 8.3 to 9.5), tris-borate (range of pH 7.0 to 8.5), tris-acetate (range of pH from 7.2 to 8.5), TBE (tris/boric acid/EDTA) (range of pH 8.3 to 8.6), HEPES (range of pH from 6.8 to 8.2), PIPES (range of pH from 6.1 to 7.5), TES (range of pH from 6.8 to 8.2), PBS (range of pH from 7.0 to 7.8), PB (range of pH from 7.2 to 8.2); preferably TBE (tris/boric acid/EDTA), PBS (phosphate buffered saline) and PB (potassium phosphate monobasic/disodium hydrogen phosphate dehydrate); more preferably TBE and PB, the most preferred PB. Buffer compositions are well known by the person skilled in the art. As the person skilled in the art will understand, the pH of the buffer composition is chosen depending on the isoelectric point of the compounds of the mobile phase in order to obtain a charged compound. For example, if the isoelectric point of a compound of the mobile phase is 4, the pH of the buffer composition must be higher than 4 to have the compound negatively charged and must be lower than 4 to have the compound positively charged. Buffer most appropriate for culturing cells is PB. A suitable composition for PB is 2.6 mM potassium phosphate monobasic and 7.3 mM disodium hydrogen phosphate dehydrate having pH 7.4 and ionic strength of 24 mM.

The components of the mobile phase are in native state. By "native", as used herein, it is meant that the method of the invention is made in absence of any denaturing agent. In native conditions proteins migrate as a function of their charge, size and shape and interactions between subunits are maintained. In native conditions proteins preserve their function as is expected for a biomimetic scaffold.

This technique uses a direct current electric field applied in a closed circuit to move and position bioactive molecules to create reproducible well organized patterns within hydrogel materials in 3D.

The term "direct current" or "DC", as used herein, refers to the unidirectional flow of electric charge. The electric charge flows in a constant direction, distinguishing it from alternating current.

The term "electric field", as used herein, refers to the field that surrounds electrically charged particles and time-varying magnetic fields.

The term "closed circuit", as used herein, refers to an electric circuit providing an uninterrupted, endless path for the flow of current.

By applying an electric field, the molecules and/or macromolecular entities contained in the mobile phase will move through the hydrogel toward the anode if negatively charged or toward the cathode if positively charged. Therefore, the method of the invention is useful for both positively and negatively charged molecules. The person skilled in the art can reverse the polarity of the electric field applied depending on the charge of the molecules and/or macromolecular entities contained in the mobile phase.

Since overheating is a potential problem, a method of heat removal should be supplied (a circulating thermostated bath or cold tap water) to prevent heat-induced artifacts or damage. Therefore, this step may be submitted to temperature control.

To perform the method of the invention, a typical system for vertical or horizontal protein electrophoresis may be used. However, the method of the invention uses an electrical insulating material and thus relies in the dielectrophoretic principle, specifically in the insulator-based direct current dielectrophoresis (DC-iDEP), which uses insulating obstacles to create spatial field nonuniformities.

Dielectrophoresis refers to the force that is used to move the molecules and/or macromolecular entities of the mobile phase through the hydrogel matrix when said entities are subjected to a nonuniform electric field.

In this circuit, voltage and current are supplied by a DC power supply; the leads, electrodes, buffer and hydrogel all act as simple resistors.

Power supplies used in the present invention hold one electrical parameter (current, voltage, or power) constant. The resistance of the dielectrophoresis circuit, however, does not remain constant during a run.

The dielectrophoresis (DEP) force experienced by the mobile phase depends on the permittivity of the medium surrounding it ($\in_m$), the electric field (E), the radius of each particle (r) contained in the mobile phase, and the dielectric properties of the buffer and the particle, which are traditionally described by the Clausius-Mossotti (CM) factor, α:

$$(\vec{F})_{DEP} = 2\pi r^3 \in_m \alpha (\nabla \vec{E}^2)$$

where α:

$$\alpha = \frac{\sigma_p - \sigma_m}{\sigma_p + 2\sigma_m}$$

wherein $\sigma_p$ is the conductivity of a particle and $\sigma_m$ is the conductivity of the buffer.

The conductivity of a particle ($\sigma_p$) can be expressed as a function of the surface conductivity $\kappa_s$, the bulk conductivity within the particle $\sigma_b$, and the particle radius (r) [the particle is considered spherical to reduce complexity in the problem], as shown below:

$$\sigma_p = \sigma_b + \frac{2\kappa_s}{r}$$

An explanation of the dielectrophoretic principle may be found on Srivastava S. K. et al. (Soumya K. Srivastava & Aytug Gencoglu &Adrienne R. Minerick. DC insulator dielectrophoretic applications in microdevice technology: a review. Anal Bioanal Chem (2011) 399:301-321).

Although a typical system for protein electrophoresis may be used, the method of the invention differs from the classical electrophoresis since molecules are not separated by their molecular weight and the electrical field is modified by using an electrical insulating material.

When the electric field is applied, step (c) of the method of the invention starts. This step consists of patterning the immobile phase with the components of the mobile phase, in which said components move by forming patterns within the immobile phase and are not separated by their molecular weight and in which the location of the components of the mobile phase is controlled as desired by modulating the electric field and the time.

One of the characteristic features of this method is that the mobile phase is patterned within the immobile phase.

"Patterning" or "move by forming patterns", as used herein, relates to drawing a continuous path in the hydrogel with the molecules and/or macromolecular entities of the mobile phase. The molecules are homogeneously distributed along the path or distributed along the path forming a gradient and are not separated by their molecular weight or concentrated in a specific location. The molecules or macromolecular entities contained in the mobile phase are finally immobilized within the hydrogel.

The homogeneous or gradient patterns may be obtained by conventional methods known by the skilled person in the art.

According to the method of the invention the components of the mobile phase are positioned in specific locations within the hydrogel to create a complex in vivo-like environment.

The "components of the mobile phase", as used herein, refers to the charged compounds and/or charged macromolecular entities that form part of the mobile phase.

The expression "are not separated by their molecular weight", as used herein, means that the resulting hydrogel is different from a hydrogel obtained in classical electrophoresis, when molecules are separated by their molecular weight, i.e. proteins are resolved. The term "molecular weight", as used herein, refers to the sum of the atomic weights of all the atoms in a molecule. When the molecule is a peptide or a protein the molecular weight is expressed in Daltons.

The expression "location of the components of the mobile phase", as used herein, refers to the specific pattern obtained in the hydrogel formed by the mobile phase. Different factors are involved in the final location of the components of the mobile phase through the hydrogel. Specifically, the location of the components depends on the molecular size and charge of the mobile phase, the porosity of the immobile phase, the dimension and position of the insulating material and the modulation of the electrical field and the time during which the mobile phase is patterned through the immobile phase. The person skilled in the art knows how to modify said parameters to locate the components of the mobile phase in the location desired.

For example, the velocity of migration of the components of the mobile phase through the gel is affected directly by the molecular size of said components. Components having a small molecular size move faster and migrate further than components with a big molecular size. The overall charge of a component also affects the speed at which it moves through the hydrogel. The charge of the mobile phase is due to the buffer pH. Therefore, small molecular size and strong charge increase the migration rate of the component through the hydrogel, whereas large size and weak charge decreases the migration rate.

The porosity of the immobile phase also affects the final location of the components of the mobile phase. The pore size and sieving characteristics of a hydrogel can be controlled by adjusting the concentration of the polymer (agarose, chitosan, gelatin, etc.). The higher the concentration, the smaller the pore size.

The dimension and position of the insulating material, as previously disclosed, is another important parameter that allows controlling the final location of the molecules of the mobile phase.

The expression "is controlled as desired", as used herein, means that the operator that puts into practice the method of the invention can decide in which part of the immobile phase is to be patterned each mobile phase. To achieve this, the operator may modify some variables such as the electric field or the time that the electric field is applied. The use of electrical insulating materials, and the specific design of the porous membrane may be changed to obtain the desired pattern. The person skilled in the art may predict the pattern obtained by using simulations in computer programs such as COMSOL Multiphysics, as is disclosed in the Examples.

The expression "modulating the electric field", as used herein, includes any modulation of the electric field that may be performed by the use of an electrical insulating material or by the modification of the level of constant current or constant voltage. The dimension and position of the electrical insulating material allows modulating the electrical field. The term "voltage", as used herein, refers to the potential difference between two points. The voltage is denoted $\Delta V$ and is measured in volts or Joules per Coulomb. A voltimeter can be used to measure the voltage between two points in a system. Section 2.2 of the Examples show curved patterned lines obtained when the electrical field is affected. The electrical field is also modulated by the use of a cooling system.

The expression "modulating the time", as used herein, means that the operator may decide the time during which the voltage is applied. Time may be measured in seconds, minutes or hours.

When the 3D-patterning method is finished, the hydrogel is removed from the mold used for performing the method and is ready for use.

The method of the invention may be performed under sterile conditions, for example when the mobile phase contains cells. In such conditions sterilized materials are required. Methods for sterilizing are well known by the person skilled in the art. Therefore, in a preferred embodiment, the method is performed under sterile conditions.

To confirm the results the hydrogel may be stained. Staining methods include dye-binding (e.g. Coomassie Brilliant Blue) or silver stains. Another possibility to confirm the pattern obtained is to use fluorescently labeled proteins in the mobile phase.

Thus, the 3D-patterning method of the invention allows controlling with high precision and reproducibility the positioning and presentation of different molecules and/or macromolecular entities inside the scaffold allowing constructing scaffolds with programmed spatial features for tissue engineering or other applications.

The 3D biomimetic scaffold of the invention may be used as such or may be cut into fragments for different applications.

The 3D biomimetic scaffold of the invention may include cells, specifically live cells. Cells may be on the 3D biomimetic scaffold because they have been included before the polymerization of the hydrogel or because they have been patterned as forming part of the mobile phase. Said cells may be cultured directly on the biomimetic scaffold. In addition, cells may be cultured on the surface of the scaffold. Specifically, the 3D biomimetic scaffold obtained by the method of the invention may be cut into pieces and each piece may be used as support for cell growth. Thus, in a preferred embodiment the method further comprises culturing cells in or on the product resulting from step c) or a fragment thereof.

The expression "culturing cells" refers to submit cells to the conditions suitable for maintaining them viable while growing and spreading over the scaffold. Conditions for culturing cells are well known by the person skilled in the art and will vary depending on the specific type of cell cultured. In general, the 3D structure is seeded with cells and cultured for a period of time with suitable culture media, preferably until the entire structure is coated with living cells. Said living cells are capable of migrating through the 3D scaffold following the pattern obtained by the method of the invention.

Thus, for engineering tisssue or regenerative medicine cells may be seeded within a scaffold that defines the geometry of the replacement tissue and provides environmental cues that promote tissue regeneration.

The term "cell", as used herein, relates to any kind of cell. Useful cells for this invention are, without limitation, primary cells such as endothelial cells, mesenchymal stem cells, osteoblasts, chondrocytes and neurons; cell lines such as HeLa, DU145, LNCaP, MCF-7, MDA-MB-438, PC3, T47D, THP-1, U87, SH-SY5Y, Saos-2, Vero, GH3, PC12, MC3T3, Tobacco BY-2, Zebrafish ZF4, Zebrafish AB9, MDCK, Xenopus A6, 293-T, 3T3, 721, 9L, A-549, A172, A20, A253, A2780, A2780ADR, A2780cis, A431, ALC, B16, B35, BCP-1, BEAS-2B, bEnd.3, BHK-21, BR 293, BxPC3, C2C12, C3H-10T1/2, C6/36, Cal-27, CHO, CML T1, CMT, COR-L23, COR-L23/5010, COR-L23/CPR, COR-L23/R23, COS-7, COV-434, CT26, D17, DH82, DuCaP, EL4, EM2, EM3, EMT6/AR1, EMT6/AR10.0, FM3, H1299, H69, HB54, HB55, HCA2, HEK-293, Hepa1c1c7, BTI-TN-5B1-4, HL-60, HMEC, HT-29, J558L, Jurkat, JY, K562, KCL22, KG1, Ku812, KYO1, LNCap, Ma-Mel cells, MC-38, MCF-10A, MCF-7, MDA-MB-231, MDA-MB-435, MDA-MB-468, MDCK II, MG63, MONO-MAC 6, MOR/0.2R, MRCS, MTD-1A, MyEnd, NALM-1, NCI-H69/CPR, NCI-H69/LX10, NCI-H69/LX20, NCI-H69/LX4, NIH-3T3, NALM-1, NW-145, OPCN/OPCT cell lines, PNT-1A/PNT 2, Raji, RBL, RenCa, RIN-5F, RMA/RMAS, Sf21, Sf9, SiHa, SkBr3, T-47D, T2, T84, THP1, U373, U87, U937, VCaP, WM39, WT-49, X63, YAC-1 and YAR; preferably stem cells, more preferably mesenchymal stem cells. When the 3D biomimetic scaffold is going to be used in therapy, the cells preferably are autologous cells, i.e. from the same patient to which the 3D biomimetic scaffold is going to be administered or implanted.

The expression "product resulting from step c)", as used herein, refers to the whole 3D biomimetic scaffold as is obtained from the method of the invention. Cells cultured may be those cells being inside the biomimetic scaffold or those cells deposited on the surface of the biomimetic scaffold.

Figure 3:
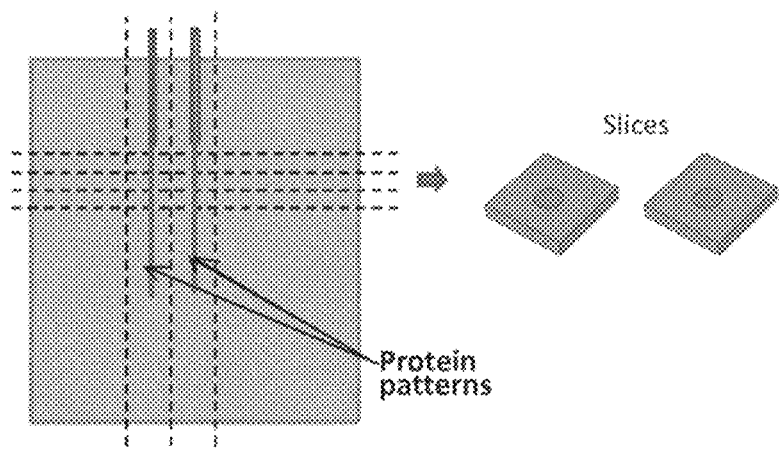
FIG. 3. Diagram showing the method for obtaining slices of patterned agarose from the 3D biomimetic scaffold of the invention. Each dot line in the immobile phase indicates the cut.

A "fragment" of the biomimetic scaffold, as used herein, is a piece of the biomimetic scaffold, either longitudinal or transversal, preferably a transversal piece, that has been obtained after cutting the whole biomimetic scaffold obtained by the method of the invention (FIG. 3). In a preferred embodiment, cells are seeded on the surface of a fragment of the biomimetic scaffold and are cultured on top of it, as is showed on section 1.4.1 of the Examples.

FIG. 1 schematically shows the components of the method of the invention for manufacturing 3D biomimetic scaffolds in accordance with different embodiments. In a particular embodiment (FIG. 1(A)), a porous membrane (3) is used as electrical insulating material; in this embodiment, a mobile phase (1) comprising a solution of molecules passes through a porous membrane (3) in order to pattern an immobile phase(2) (FIG. 1 (A), left); then the device is submerged in a buffer (8) inside a chamber (5) having two electrodes (6) and (7) and patterns are formed according to the method of the invention—the arrows indicate the direction in which the mobile phase (1) runs (FIG. 1 (A), right). In another embodiment (FIG. 1(B)) tubes (4) filled with proteins as electrical insulating material are used; in this embodiment, tubes (4) are filled with mobile phase (1) in order to pattern an immobile phase (2) (FIG. 1 (B), left) ; then the device is submerged in a buffer (8) inside a chamber (5) having two electrodes (6) and (7) and patterns are formed according to the method of the invention.

3D Biomimetic Scaffold of the Invention

A second aspect of the present invention relates to a three-dimensional (3D) biomimetic scaffold obtainable by the method of the invention described above (hereinafter, 3D biomimetic scaffold of the invention) or a fragment thereof.

In a preferred embodiment of this second aspect of the invention, the 3D biomimetic scaffold is a replacing tissue. This technique can be applied to studies or therapies to regenerate any kind of tissue such as bone, cartilage, skin, ligament, tendon, neural, cardiac, muscle, enamel, hepatic, epithelial and corneal tissue. In a preferred embodiment the replacing structure is an intervertebral disc. In another preferred embodiment the replacing structure is an orosteochondral segment.

The 3D biomimetic scaffold of the invention can be cut into the desired size and/or can be provided in a suitable conformation for use.

Therapeutic Uses of the 3D Biomimetic Scaffold of the Invention

The extracellular matrix contains many macromolecules such as proteoglycans, collagens, laminins, fibronectin and sequestered growth factors, and it is primarily this molecular information that confers its bioactivity.

The 3D biomimetic scaffold of the invention is useful in tissue engineering for facilitating recreation of complex 3D tissues or environments to guide cells and create tissues in vitro.

In tissue engineering, the application of growth factors within biomaterials also represents a powerful tool for controlling cell differentiation and function. For example, the patterning of growth factors within prefabricated scaffolds could aid the generation of heterogeneous tissues.

These biomimetic scaffolds can be directly implanted in patients or may be used to expand and guide cell populations that are subsequently delivered and implanted into areas that require large cell populations.

The biomimetic scaffolds of the invention are also useful in regenerative medicine since they can be implanted at the site of injury without including cells. Examples of suitable scaffolds for regenerative medicine may be intervertebral discs or orosteochondral segments or other kind of scaffolds for spinal cord regeneration.

An infectious, inflammatory, genetic or degenerative disease, physical or chemical damage, or blood flow interruption, can cause degeneration, damage or loss of a tissue. This would lead to an alteration of the normal function of said tissue; and consequently lead to the development of diseases or physical consequences reducing the person's quality of life. Therefore, attempting to regenerate or reestablish the normal function of said tissues is important. The damaged tissue can be replaced by a new tissue which has been produced in the laboratory by means of tissue engineering techniques. The objective of tissue engineering is to construct artificial biological tissues and to use them for medical purposes to restore, replace or increase the functional activities of diseased tissues. The therapeutic use of techniques of this type is virtually unlimited with applications in all fields. The use of tissue engineering techniques allows reducing the waiting lists for tissues and organs, with the consequent reduction of the disease morbidity-mortality in recipient. As a consequence, it also logically reduces the morbidity-mortality in organ donors. In addition, there are many advantages associated with the use of autologous cells or tissues in tissue engineering, which include: (a) a significant reduction of the number of infections from the donor to the recipient by infectious agents; and (b) the absence of host immune graft rejection, therefore the patient does not need to undergo immunosuppressing treatment, side effects and problems associated with immunodepression being prevented.

The method of the invention is particularly useful in tissue engineering and regenerative medicine.

Therefore, another aspect of the invention relates to a three-dimensional (3D) biomimetic scaffold of the invention or a three-dimensional (3D) biomimetic scaffold obtained according to the method of the invention or a fragment thereof for use in medicine.

Another aspect of the invention relates to a three-dimensional (3D) biomimetic scaffold of the invention or a three-dimensional (3D) biomimetic scaffold obtained according to the method of the invention or a fragment thereof for use in the replacement, reparation or regeneration of a damaged, dysfunctional or pathological tissue. In another aspect, the invention relates to the use of a three-dimensional (3D) biomimetic scaffold of the invention or a three-dimensional (3D) biomimetic scaffold obtained according to the method of the invention or a fragment thereof to replace, repair or regenerate a damaged, dysfunctional or pathological tissue. In another aspect, the invention relates to a method of treatment for replacing, repairing or regenerating a damaged, dysfunctional or pathological tissue comprising the administration of a 3D biomimetic scaffold of the invention or a 3D biomimetic scaffold obtained according to the method of the invention or a fragment thereof.

The biomimetic scaffold of the invention can be used to replace, repair or regenerate a damaged, dysfunctional or pathological tissue of a living organism. The tissue can be an internal tissue such as, for example, but not limited to, an intervertebral disc, an orosteochondral segment, cardiac, cartilage, connective, muscular, vascular, nerve, adipose, hepatic, pancreatic, bone, glandular or epithelial tissue; or external tissue such as, for example, but not limited to, cornea, skin, enamel or epithelial squamous tissue. In a preferred embodiment, the damaged tissue is selected from the list comprising: skin, bladder, urethra, cornea, mucosa, conjunctiva, abdominal wall, eardrum, pharynx, larynx, intestine, peritoneum, ligament, tendon, bone, meninx or vagina. The tissue can be diseased or damaged as a result of a dysfunction, an injury or a disease, for example, but not limited to, an infectious disease, an inflammatory disease, a genetic disease or a degenerative disease; physical damage such as a traumatism or a surgical intervention, a chemical damage or blood flow interruption.

Another aspect of the present invention relates to the use of the 3D biomimetic scaffold of the invention for preparing a medicament.

Said medicament is a medicament for somatic cell therapy. "Somatic cell therapy" is understood as the use of living, autologous, allogenic or xenogenic somatic cells, the biological characteristic of which have been substantially altered as a result of their manipulation for obtaining a therapeutic, diagnostic or preventive effect through metabolic, pharmacological or immunological means. Among the medicaments for somatic cell therapy are, for example, but not limited to: cells manipulated to modify their immunological, metabolic or other type of functional properties in qualitative and quantitative aspects; sorted, selected and manipulated cells which are subsequently subjected to a manufacturing process for the purpose of obtaining the end product; cells manipulated and combined with non-cellular components (for example, biological or inert matrices or medical devices) performing the principle intended action in the finished product; autologous cell derivatives expressed ex vivo (in vitro) under specific culture conditions; cells which are genetically modified or are subjected to another type of manipulation to express homologous or non-homologous functional properties not expressed before. Thus, in another aspect, the invention relates to the use of a three-dimensional (3D) biomimetic scaffold of the invention or a three-dimensional (3D) biomimetic scaffold obtained according to the method of the invention or a fragment thereof for manufacturing a medicament to replace, repair or regenerate a damaged, dysfunctional or pathological tissue.

Another aspect of the invention relates to a pharmaceutical composition comprising the 3D biomimetic scaffold of the invention or a 3D biomimetic scaffold obtained according to the method of the invention or a fragment thereof. In a preferred embodiment said pharmaceutical composition is for use in somatic cell therapy, more preferably to replace, repair or regenerate a damaged, dysfunctional or pathological tissue.

In a preferred embodiment of this aspect of the invention, the pharmaceutical composition comprises the 3D biomimetic scaffold of the invention, or a 3D biomimetic scaffold obtained according to the method of the invention or a fragment thereof and also a pharmaceutically acceptable carrier. In another preferred embodiment the pharmaceutical composition comprises the 3D biomimetic scaffold of the invention or the 3D biomimetic scaffold obtained according to the method of the invention or a fragment thereof and also another active ingredient. In a preferred embodiment, the pharmaceutical composition comprises the 3D biomimetic scaffold of the invention or a 3D biomimetic scaffold obtained according to the method of the invention or a fragment thereof and also another active ingredient together with a pharmaceutically acceptable carrier.

As used herein, the term "active ingredient", "active substance", "pharmaceutically active substance" or "pharmaceutically active ingredient" means any component which potentially provides a pharmacological activity or another different effect in diagnosing, curing, mitigating, treating, or preventing a disease, or which affects the structure or function of the human body or body of other animals.

The pharmaceutical compositions of the present invention can be used in a treatment method in an isolated manner or together with other pharmaceutical compounds.

Non-Therapeutic Uses of the 3D Biomimetic Scaffold of the Invention

Since the 3D biomimetic scaffold of the invention may recreate the in vivo environment, it is useful as a model to screen for active drugs. This allows minimizing the use of animal testing since compounds may be assayed in vitro with higher reliability.

Thus, another aspect relates to the use of a three-dimensional (3D) biomimetic scaffold of the invention or of a three-dimensional (3D) biomimetic scaffold obtained according to the method of the invention or a fragment thereof as an in vivo-like model for drug screening.

Furthermore, said technology will allow for the fabrication of devices that can be used to test drugs using high-throughput screening. For example, by using different biomimetic scaffolds designed to have different patterns.

In addition, formation of the extracellular matrix is essential for processes like growth, wound healing and fibrosis. An understanding of ECM structure and composition also helps in comprehending the complex dynamics of tumor invasion and metastasis in cancer biology as metastasis often involves the destruction of extracellular matrix by enzymes such as serine and threonine proteases and matrix metalloproteinases. Thus, another aspect relates to the use of a three-dimensional (3D) biomimetic scaffold of the invention or of a three-dimensional (3D) biomimetic scaffold obtained according to the method of the invention or a fragment thereof as a model for molecular or cell biology studies. The expression "model for molecular or cell biology studies" means that the 3D biomimetic scaffold of the invention is useful to study in vitro the complex environment present in different biological tissues, developmental processes, or pathological conditions. In particular, said molecular or cell biology studies may be related to the study of cancer metastasis, embryogenesis, studies of binding, spinal cord regeneration, etc. For example, to study factors that favor the migration of a cancer cell, or factors that favor the regeneration of the axon of a neurone.

As previously explained, the 3D biomimetic scaffold of the invention is capable of supporting cell growth. Cells may be cultured on the surface of a fragment of the hydrogel. Alternatively, cells are encapsulated in the polymerizable material prior to polymerization. Alternatively, cells may be patterned using the method of the invention. Therefore, another aspect of the invention is the use of a three-dimensional (3D) biomimetic scaffold of the invention or of a three-dimensional (3D) biomimetic scaffold obtained according to the method of the invention or a fragment thereof to support cell growth.

The invention is described below by means of several examples which do not limit, but rather illustrate the invention.

EXAMPLES

The following examples describe the production of 3D biomimetic scaffolds based on the application of an electrical field to a polymerized hydrogel material to pattern different molecules.

1. Materials and Methods 1.1 Parts of the Method of the Invention

By using an electrical field, the method of the invention is able to move and position bioactive molecules (such as peptides, proteins, dendrimers, etc.) within a three-dimensional (3D) space to create reproducible well organized patterns within hydrogel materials. This technique comprises four key parts as schematically depicted in the particular embodiment shown in FIGS. 1A and 1B:

Electrophoresis: This part is composed of the electrodes (6) and (7), a buffer (8) and the chamber (5) which contains the phases mobile (1) and immobile (2).

Immobile phase (2): This part is the hydrogel that is going to be patterned with the molecules.

Mobile phase (1): This part refers to the molecules that are going to pattern the hydrogel.

Mobile container: This part could be either:

Membrane (3). It serves as a mask that defines the regions through which the molecules will pass. The membrane can be easily modulated to exhibit almost any design.

Tubes (4). An alternative is to use small tubes containing the molecules. Those structures may be sufficient to define the areas where the molecules will be patterned.

1.1.1 Electrophoresis

As proof of concept, a Hoefer Mighty Small II Mini Vertical Electrophoresis System (HOEFER-SE260-10A-1.5, Hoefer Inc, USA) was used. The buffer was prepared by mixing in 1,000 ml of miliQ water, 0.0026 mol of potassium phosphate monobasic as acid component (P5655, Sigma, Germany) and 0.0073 mol of di-sodium hydrogen phosphate dehydrate as basic component (1.06580.0500, Merck, USA) at room temperature (RT). This solution is called phosphate buffer (PB) and has pH 7.4 and ionic strength of 0.024 M. Another kind of buffer that has been used was Tris/Boric Acid/EDTA (TBE) (161-0770, Sigma, Germany).

1.1.2 Immobile Phase

To get the immobile phase (IP), the Dual Gel Caster (DGC) (Hoefer Inc, USA) was used wherein a 2% melted agarose solution was added. The agarose solution was prepared by mixing 2% Agarose D1 Low EEO (8014, Pronadisa, Italy) to the either PB or TBE. The DGC was modified by, instead of using the regular spacers, using two plastic bars that were 5 mm wide, 100 mm long, and 5 mm high. To get the space where the mobile container was located on the IP, two different structures were used. The first one was a rectangular piece of polydimethylsiloxane (PDMS) (Sylgard 184, Dow Corning, USA) that was 1 cm high, 0.5 cm wide, and 9 cm long. The second structure was a series of plugged tubes. Two kinds of tubes were used: a) the first one was a crystal tube with an outside diameter of 0.8 mm, an inside diameter of 0.6 mm and 32 mm long (1605 BCRS, Vitrex Medical, Denmark) which was plugged by heating, and b) the second one was a plastic tube with an outside diameter of 1 mm and 15 mm long which was plugged by filling it with PDMS. Each tube was placed by one of its ends in a rectangular piece of PDMS having 0.5 cm high, 0.5 cm wide and 9 cm long. Meanwhile the IP was liquid the structure with the tubes was positioned on the top of the liquid IP placed into the DGC. IP could be any kind of hydrogel such as Polyacrylamide, Chitosan, PureMatrix, Alginate, Gelatin, etc. As proof of concept, agarose was used because it is easy to handle and permits cell culture (Mercey E. et al. 2010. Biomaterials, 31: 3156-3165).

1.1.3 Mobile Phase

The mobile phase (MP) consists of two parts including: a) the molecules that will be patterned, and b) a loading buffer, which is the solution that contains the molecules and provides the MP with the right density for running the molecules. For the molecules, as proof of concept, a solution of Elastin-Like Polymers (ELPs) (SEQ ID NO: 1) was used (isoelectric point=4.3). These molecules were not charged previously because at pH 7.4 they were already charged negatively. The ELPs consist of repeating pentapeptide domains of the amino acids VPGIG and VPGVG with the cell binding sequence RGDS (Tejeda-Montes E. et al. 2012. Acta Biomaterialia, 8(3): 998-1009). This ELP solution was made by mixing 50 mg of ELP in 1 ml of PBS. In addition, a fluorescent protein (FP) (18772, Sigma-Aldrich, Germany) was also used to be able to visualize the ELPs running in real time. It is important to keep in mind that it is possible to use other molecules such as peptides, proteins, or dendrimers. Regarding the loading buffer, two different approaches were tested. In the first one, a 2% low melting agarose (LMA) (8053, Pronadisa, Italy) solution was prepared in 10 ml of either PB or TBE. This solution was heated up to its melting point (about 65° C.) in a microwave and then allowed to cool down to 37° C., after which 200 µl of this solution were added into a 200 µl solution of the ELP. The final solution was kept above the LMA gelling point (about 26° C.) prior to be used. In the second one, the use of LMA was avoided by using glycerol (G8773, Sigma-Aldrich, Germany) instead. For example, 100 µA of glycerol were added to 1 ml of buffer. In this case, the solution was prepared by adding 50% of the ELP solution into 1 ml of either PB or TBE.

1.1.4 Mobile Container

Figure 2:
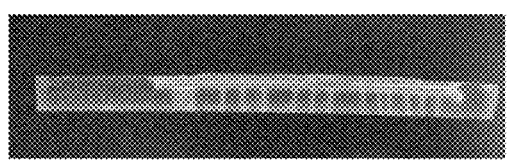
FIG. 2. Photography of a polydimethylsiloxane (PDMS) membrane with a horizontal cylindrical container to keep the mobile phase and 12 cylindrical holes with different sizes.

Two kinds of mobile container (MC) were developed, which will give the shape of the pattern trough the immobile phase. The first one is a membrane of PDMS. This was obtained curing the PDMS polymer inside of the DGC. To get an inside chamber in the MC, a piece of plastic plugged tube was pasted horizontally, with dimensions of 1 mm outside diameter and 5 cm long, to conserve its form inside of the MC. After curing the PDMS, the membrane was dimpled manually with sharp razors (Harris Uni-Core™, Sigma-Aldrich, USA) with different diameters [0.5 mm, 0.75 mm, 1 mm (FIG. 2)]. This technique may be improved by soft lithography technique (Xia Y. and Whitesides G. M. 1998. Angewandte Chemie International Edition, 37: 550-575). The second kind of mobile containers are the tubes described before but each one unplugged. Each MC was filled by the MP solution at about 28° C. When using the membrane, 300 µl of said solution were deposited inside the chambers of the membrane, while the 1 mm outside diameter tubes were filled with 50 µl using a Hamilton syringe and the 0.6 mm inside diameter tubes were filled by capillarity with 9 µl of the solution. After the tubes were filled, they were allowed to cool down to room temperature. When the MP was made, the tubes and the membrane were placed on the IP after it was gelled. Hence each tube was filled by a 20 µl Hamilton Syringe with the MP without LMA.

1.2 Running the Gel

To run an IP, each MC was placed on the hole already done with the "like-brush" structure, the electrophoresis chamber (EC) was connected to a cooler system and cold water around 1° C. was bombed through the system to cooler out. Also the EC was put inside of an icebox to keep it at 4° C. The EC was feed with an (PS 304 II, Apelex, France) power supply setup to 90 mA and 200 V. The gel was run for 90 minutes, reaching at the end an inside temperature of 33° C., at 140 V and 90 mA.

1.3 Protein Staining

After running the gel, the molecules were stained with a Coomassie blue colloidal solution, made with brilliant blue G (B0770, Sigma-Aldrich, Germany), following the protocol from Simpson R. J. (Proteins and Proteomics. A laboratory manual. Cold Spring Harbor Laboratory Press. USA. 2003).

1.4 Cell Culture

Rat mesenchymal stem cells (MSCs) were extracted and isolated from rat tibia and femur bone marrow. The bones were provided by the Animal Research Center of the Parc Cientific Barcelona. Cells were expanded in Dubelcco's modified Eagle's medium (DMEM; Invitrogen, Spain), supplemented with 10% fetal bovine serum (FBS; Attendbio, Spain), 1% glutamine (Sigma-Aldrich, Spain) and 1% penicillin/streptomycin (Sigma-Aldrich, Spain). Rat MSCs of passage 5-6 were diluted in serum free DMEM and seeded at 95,000 cell/cm$^2$ onto the pieces of running agarose with the pattern. Each piece was set to keep the cell next to the patterned area. After 2 and 4 hours, each culture was observed for finding a circular pattern and cell spreading.

1.4.1 Cell Culture Set Up

Figure 4:
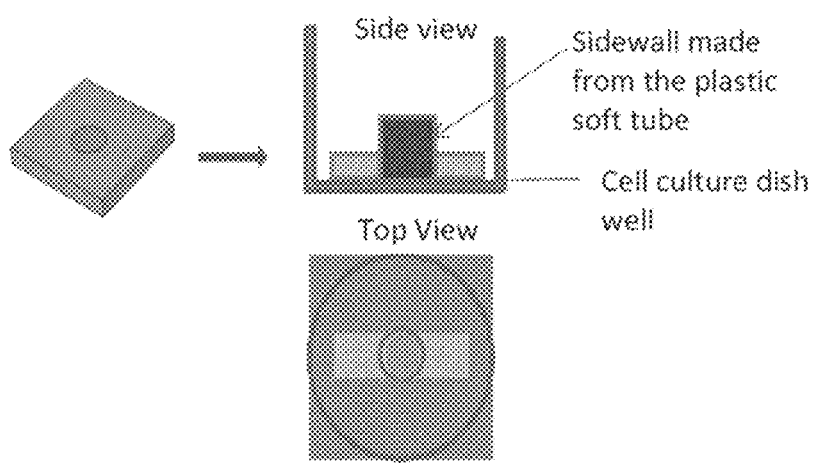
FIG. 4. Diagram showing the method for conducting the cell culture experiments on slices of patterned agarose obtained from the 3D biomimetic scaffold of the invention. The patterned agarose sample is placed inside a culture dish and a soft plastic tube is inserted into the gel piece to provide side walls for the cells and the culture media.

Cell culture was performed using 24 well plates containing the patterned samples. The IP was cut perpendicular to the patterns into multiple pieces as shown in FIG. 3. These thin slices of the IP comprising the molecular patterns were placed inside of each well for cell culture. Each slice was extracted from different levels of the cylindrical pattern and placed on each well of the 24 well plate. To hold the cells on top of the slices of gel, a piece of a soft plastic tube was inserted into the gel piece (FIG. 4) to provide "walls" so that the culture medium and cells could be inoculated and cultured on top of the gel slices. Finally, the cells were inoculated and cultured.

1.5 Membrane Simulation

Figure 5:
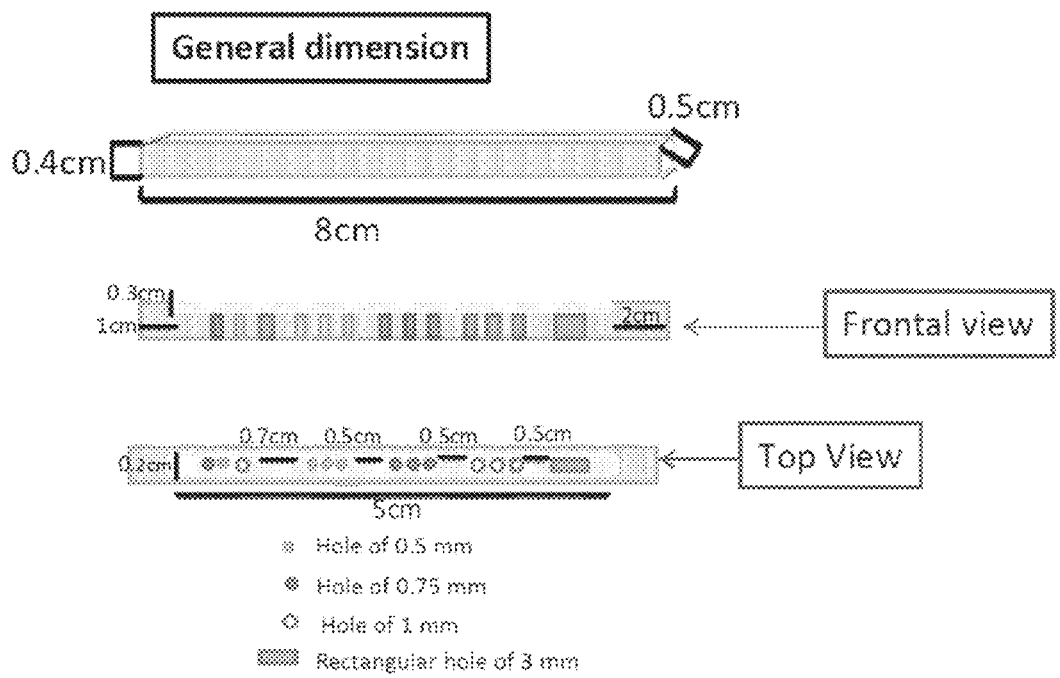
FIG. 5. Membrane model used for the simulation by COMSOL Multiphysics. The diagram shows the general dimensions, a frontal view and a top view of the membrane showing distances between holes.

Due to the fact that the presence of the membrane modified drastically the electrical field and the limitation of the hardware that has been used, the membrane model was presented by simulation in COMSOL Multiphysics 4.1, to simplify the study of the electrical field induced in the electrophoresis system. For this simulation a model of the membrane presented in FIG. 5 and an IP with TBE were used. The summary and description of the dimensions and materials are summarized in Table 1.

TABLE 1

List of the parameters with their values used in the COMSOL simulation

| Parameter | Value |
| --- | --- |
| width | 8 cm |
| thickness | 0.5 cm |
| height | 8 cm |
| h_stencil | 0.1 cm |
| w_well | 5 cm |
| x_well | 1 cm |
| t_well | 0.2 cm |
| h_well | 0.2 cm |
| r1 | 0.25 mm |
| r2 | 0.375 mm |
| r3 | 0.5 mm |
| gap1 | 0.5 cm |
| gap2 | 0.7 cm |
| spacing | 0.1 cm |
| x_block | 0.3 cm |
| y_block | 0.1 cm |
| σ (TBE) | 0.355 S/m |
| σ (PDMS) | $2.5 \cdot 10^{-14}$ S/m |
| $\epsilon_r$ (TBE) | 1 |
| $\epsilon_r$ (PDMS) | 2.7 |

2. Results

Figure 6:
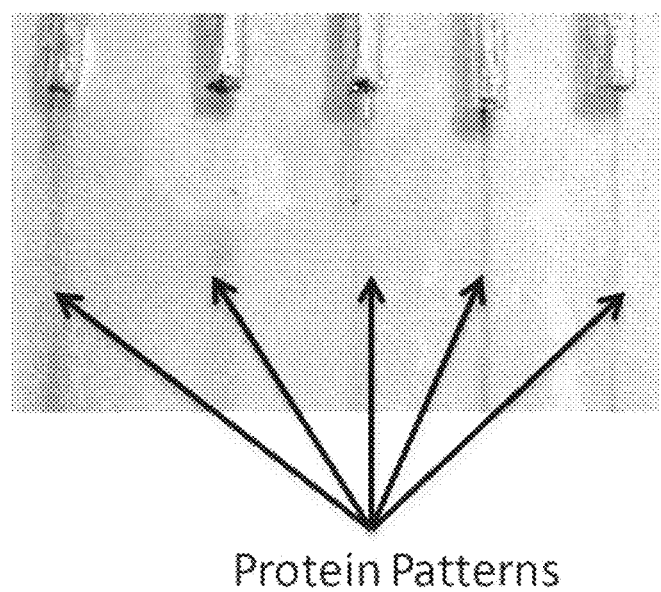
FIG. 6. Image depicting 5 cylindrical patterns of ELP-RGDS molecules obtained by the method of the invention using tubes on an agarose gel and using TBE as a buffer. TBE: Tris/boric acid/EDTA.
Figure 7:
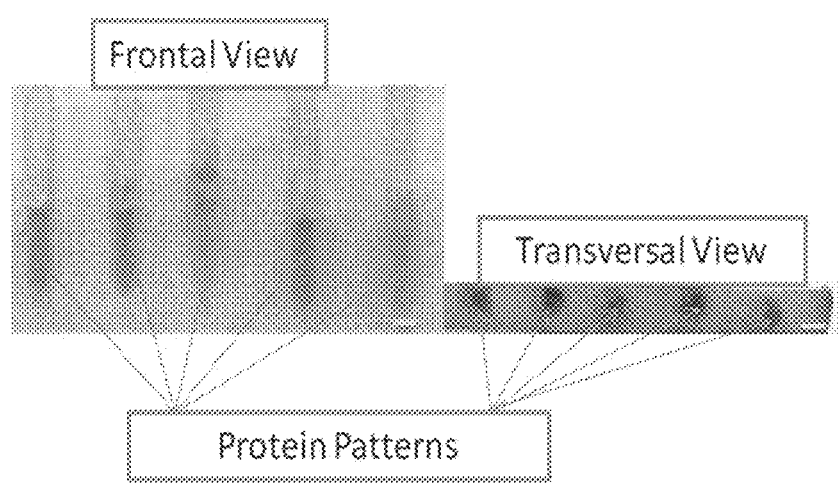
FIG. 7. Image depicting 5 cylindrical patterns of ELP-RGDS molecules obtained by the method of the invention using tubes on an agarose gel and using PB as a buffer. The picture on the left shows a frontal view of the hydrogel and the picture on the right shows a transversal cut of the patterns. Scale bar: 2 mm. PB: potassium phosphate monobasic/disodium hydrogen phosphate dehydrate.
Figure 8:
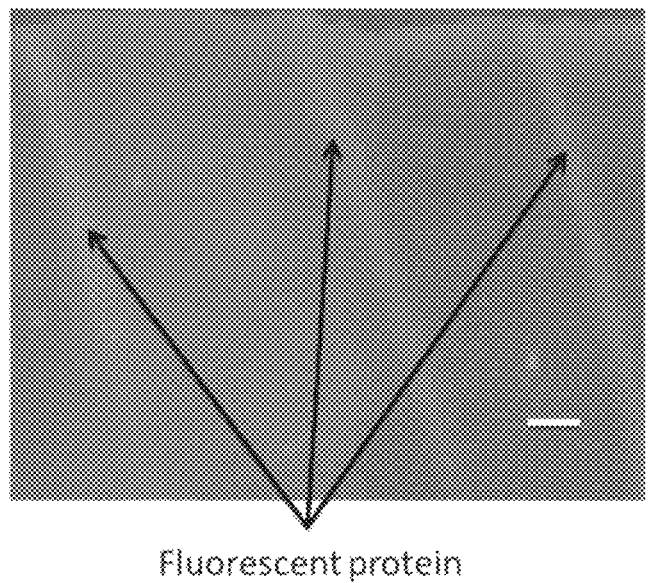
FIG. 8. Image depicting 3 cylindrical patterns of a fluorescent protein obtained by the method of the invention using tubes on an agarose gel and using PB as a buffer. Scale bar: 1 mm. PB: potassium phosphate monobasic/disodium hydrogen phosphate dehydrate.

2.1 Cylindrical Patterns without Significantly Affecting the Electrical Field For these kinds of results, the tube configuration with two kinds of buffers was used. The results of each experiment demonstrated that it is possible to achieve cylindrical patterns following the proposed patterning process. With the TBE, 5 tubes were used. Each cylindrical pattern maintained the same size as the 1 mm diameter tube (FIG. 6). The same configuration was followed with PB and, after running and staining, similar five cylindrical patterns were obtained in the gel (FIG. 7). The difference between both configurations is that with PB the gel is biocompatible and therefore it is possible to conduct cell culture experiments to determine the bioactivity of the patterned protein, because the pH and the salts of PB are appropriate for the cell environment. In another experiment, a fluorescent protein was used as MP, generating fluorescent patterns (FIG. 8) of similar dimensions.

2.2 Cylindrical Patterns Affecting the Electrical Field

Figure 9:
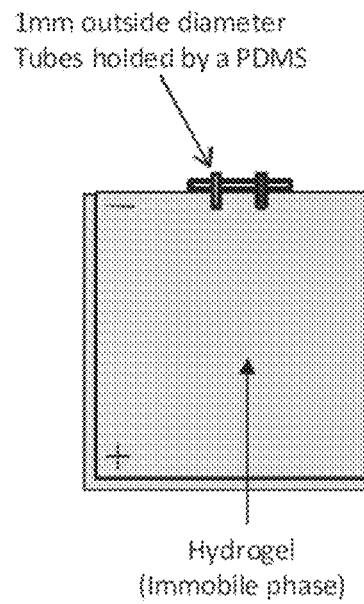
FIG. 9. Cylindrical patterns obtained by modifying the electrical field using tubes and a membrane of PDMS on an agarose gel and using PB as a buffer. Left: Diagram showing the configuration of the mobile container. Right: Resulting pattern showing curved lines due to the modification of the electrical field because the presence of the insulator polydimethylsiloxane (PDMS).

The presence of any kind of electrical insulator may modify the electrical field (Kang Y. et al. 2008. Biomed Microdevices, 10: 243-249). The method of the invention requires the presence of such materials to define the regions where the patterns will be formed. This is one of the advantages of this approach because it allows to easily modulate the geometry and regions where the patterns will be made. The existence of a piece of PDMS holding a pair of 1 mm outside diameter tubes modified the electrical field (FIG. 9).

2.3 Cell Culture on Cylindrical Patterns

Figure 10:
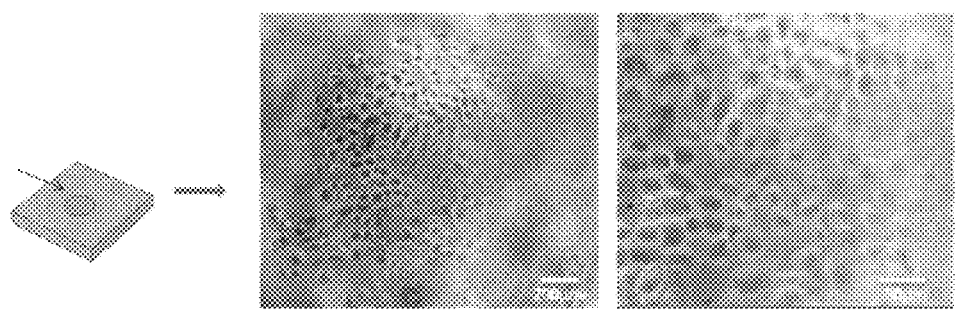
FIG. 10. Image illustrating the slice of agarose with the cylindrical pattern used as substrate for cell culture and photographs of the cells adhering and spreading on this substrate.

The cell culture experiment demonstrated that the patterns are present during cell culture and that the molecule patterned is bioactive. Cells cultured on top of the patterns attached and spread on the regions where the molecules were patterned (FIG. 10). The cells seemed to recognize the RGDS-containing ELP and attached as fast as they recognize an adhesive protein such as fibronectin on a tissue culture dish.

2.4 Membrane Simulation

Figure 11:
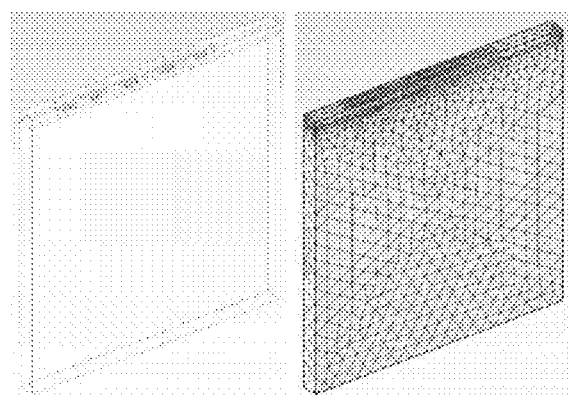
FIG. 11. COMSOL model (left) and the meshing used to get the electrical field line flux (right).
Figure 12:
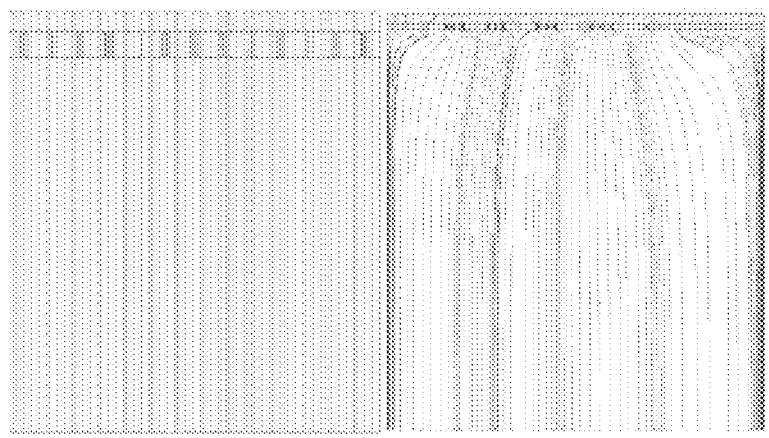
FIG. 12. Figure illustrating the electrical field without (left) and with (right) the PDMS membrane.

This solution was obtained by the meshing and the model described in the FIG. 11. After establishing the contour conditions for an electrical field analysis, the electrical field line of flux was obtained, each one modified and curved due to the presence of the insulator (the material of the membrane) in comparison with the result in the absence of it (FIG. 12).

Figure 13:
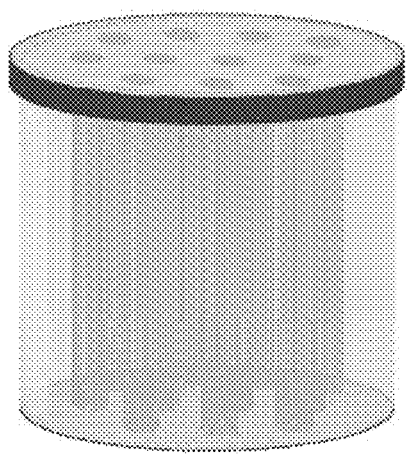
FIG. 13. Patterned 3D cylindrical-shaped hydrogel.

FIG. 13 shows a patterned 3D cylindrical-shaped hydrogel obtainable according to the method of the invention.

Figure 14:
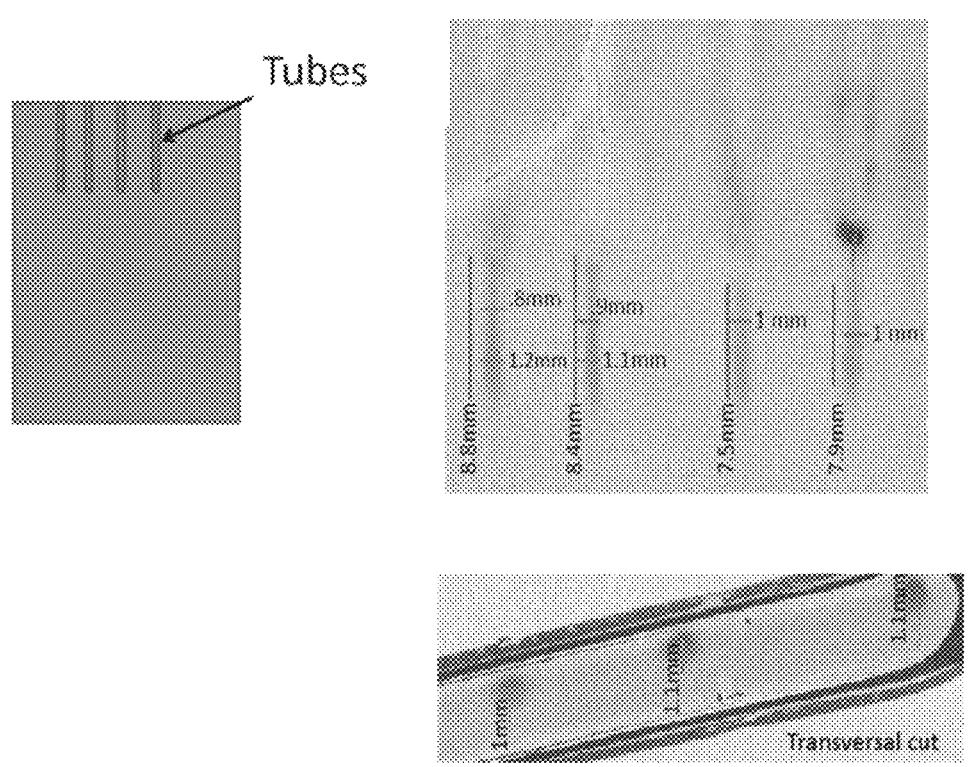
FIG. 14. Macro patterns in a vertical configuration on native polyacrylamide hydrogel obtained by the method of the invention using tubes as mobile containers and Tris-HCl as a buffer. Left: Diagram of the configuration. Right: Frontal view of a patterned gel (top) after staining with Coomassie Blue wherein vertical lines indicate the length of the protein pattern and horizontal lines indicate the width of the protein pattern. Transversal cut of a patterned gel (bottom) wherein vertical lines indicate the width of the protein pattern.

FIG. 14 shows macro patterns in a vertical configuration on native polyacrylamide hydrogel obtained by the method of the invention using tubes as mobile containers and Tris-HCl as a buffer. The diagram of the configuration is shown on the left side whereas on the right side it is shown a frontal view of the patterned gel (top) after staining with Coomassie Blue wherein vertical lines indicate the length of the protein pattern and horizontal lines indicate the width of the protein pattern. A transversal cut of the patterned gel is also shown (bottom) wherein vertical lines indicate the width of the protein pattern.

Figure 15:
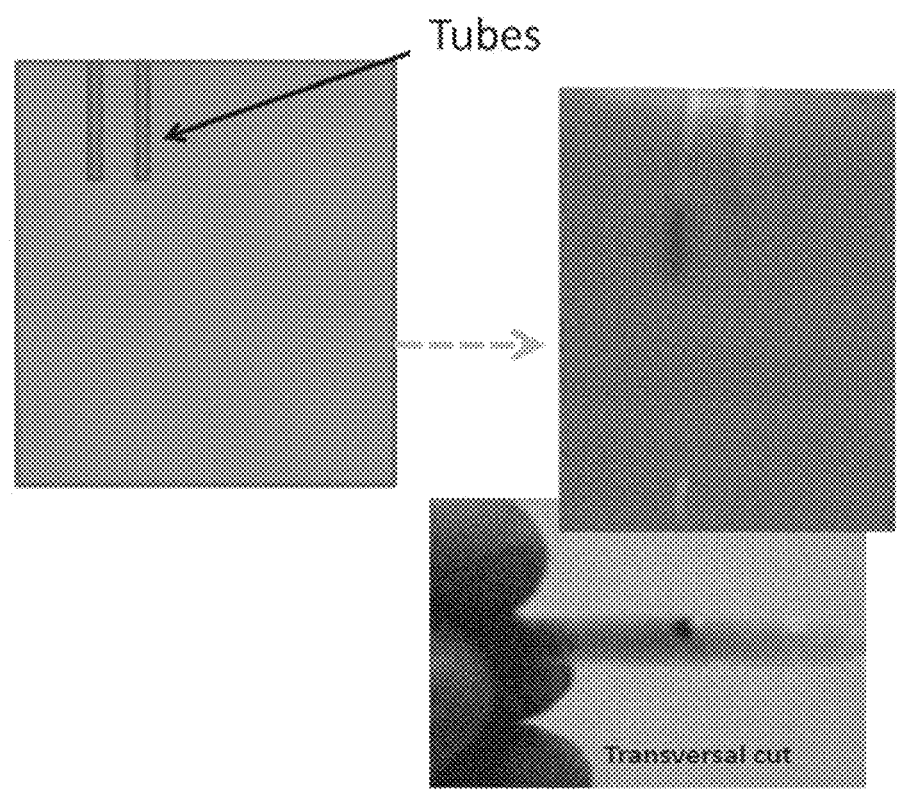
FIG. 15. Macro patterns in a vertical configuration on native agarose hydrogel obtained by the method of the invention using tubes as mobile containers and TBE as buffer. Left: Diagram of the configuration. Right: Frontal view of a patterned gel (top) and transversal cut (bottom) after staining with Coomassie Blue.

FIG. 15 shows macro patterns in a vertical configuration on native agarose hydrogel obtained by the method of the invention using tubes as mobile containers and TBE as buffer. The diagram of the configuration is shown on the left side whereas on the right side it is shown a frontal view (top) and a transversal cut (bottom) of the patterned gel after staining with Coomassie Blue.

The invention claimed is:

1. A method for manufacturing a three-dimensional (3D) biomimetic scaffold comprising:
   a) contacting a mobile phase with an immobile phase through an electrical insulating material containing the mobile phase, said electrical insulating material selected from the group consisting of:
      (i) a porous membrane placed on the surface of the top of the immobile phase, said porous membrane defining the geometrical regions through which the mobile phase passes;
      (ii) at least a tube inserted into the top of the immobile phase; and
      (iii) a combination of (i) and (ii);
   b) subjecting said mobile phase and said immobile phase in the presence of the electrical insulating material to a direct current (DC) electric field created inside a chamber and applied in closed circuit by a pair of electrodes in vertical or horizontal configuration, said chamber containing the mobile phase, the immobile phase and the electrical insulating material covered by a buffer; and
   c) patterning the immobile phase with the components of the mobile phase, in which said components move by forming patterns within the immobile phase and are not separated by their molecular weight and in which the location of the components of the mobile phase is controlled as desired by modulating the electric field and the time;
   wherein the mobile phase is an aqueous or organic medium comprising at least a charged compound and/or a charged macromolecular entity; and
   wherein the immobile phase is any previously polymerized hydrogel.

2. The method according to claim 1, wherein the compound of the mobile phase is selected from the group consisting of a peptide, a protein, a nucleic acid, a nanoparticle, a microparticle, a dendrimer or a peptide-dendrimer conjugate.

3. The method according to claim 1, wherein the compound of the mobile phase is selected from the group consisting of a hormone, a growth factor, an enzyme, a fluorescent molecule, a drug, a fluorescent molecule-dendrimer conjugate or a drug-dendrimer conjugate.

4. The method according to claim 1, wherein the macromolecular entity is a cell or a fragment thereof.

5. The method according to claim 1, wherein the hydrogel is an agarose hydrogel.

6. The method according to claim 1, wherein the hydrogel is a polyacrylamide hydrogel.

7. The method according to claim 1, wherein the geometrical regions of the porous membrane are defined by holes in said membrane.

8. The method according to claim 1, wherein the geometrical regions of the porous membrane are defined by tubes inserted in the holes of said membrane.

9. The method according to claim 1, wherein the porous membrane is a polydimethylsiloxane membrane.

* * * * *

SEQUENCE LISTING

```
<160> NUMBER OF SEQ ID NOS: 1

<210> SEQ ID NO 1
<211> LENGTH: 1331
<212> TYPE: PRT
<213> ORGANISM: Artificial Sequence
```

<220> FEATURE:
<223> OTHER INFORMATION: Elastin-like polymer (ELP)

<400> SEQUENCE: 1

```
Met Glu Ser Leu Leu Pro Val Pro Gly Val Gly Val Pro Gly Val Gly
1               5                   10                  15

Val Pro Gly Glu Gly Val Pro Gly Val Gly Val Pro Gly Val Gly Val
                20                  25                  30

Pro Gly Val Gly Val Pro Gly Val Gly Val Pro Gly Glu Gly Val Pro
            35                  40                  45

Gly Val Gly Val Pro Gly Val Gly Val Pro Gly Val Gly Val Pro Gly
        50                  55                  60

Val Gly Val Pro Gly Glu Gly Val Pro Gly Val Gly Val Pro Gly Val
65                  70                  75                  80

Gly Val Pro Gly Val Gly Val Pro Gly Val Gly Val Pro Gly Glu Gly
                85                  90                  95

Val Pro Gly Val Gly Val Pro Gly Val Gly Val Pro Gly Val Gly Val
                100                 105                 110

Pro Gly Val Gly Val Pro Gly Glu Gly Val Pro Gly Val Gly Val Pro
            115                 120                 125

Gly Val Gly Val Pro Gly Val Gly Val Pro Gly Val Gly Val Pro Gly
        130                 135                 140

Glu Gly Val Pro Gly Val Gly Val Pro Gly Val Gly Val Pro Gly Val
145                 150                 155                 160

Gly Val Pro Gly Val Gly Val Pro Gly Glu Gly Val Pro Gly Val Gly
                165                 170                 175

Val Pro Gly Val Gly Val Pro Gly Val Gly Val Pro Gly Val Gly Val
                180                 185                 190

Pro Gly Glu Gly Val Pro Gly Val Gly Val Pro Gly Val Gly Val Pro
            195                 200                 205

Gly Val Gly Val Pro Gly Val Gly Val Pro Gly Glu Gly Val Pro Gly
        210                 215                 220

Val Gly Val Pro Gly Val Gly Val Pro Gly Val Gly Val Pro Gly Val
225                 230                 235                 240

Gly Val Pro Gly Glu Gly Val Pro Gly Val Gly Val Pro Gly Val Gly
                245                 250                 255

Val Pro Gly Ile Gly Val Pro Gly Ile Gly Val Pro Gly Ile Gly Val
                260                 265                 270

Pro Gly Ile Gly Val Pro Gly Ile Gly Val Pro Gly Ile Gly Val Pro
            275                 280                 285

Gly Ile Gly Val Pro Gly Ile Gly Val Pro Gly Ile Gly Val Pro Gly
        290                 295                 300

Ile Gly Val Pro Gly Ile Gly Val Pro Gly Ile Gly Val Pro Gly Ile
305                 310                 315                 320

Gly Val Pro Gly Ile Gly Val Pro Gly Ile Gly Val Pro Gly Ile Gly
                325                 330                 335

Val Pro Gly Ile Gly Val Pro Gly Ile Gly Val Pro Gly Ile Gly Val
                340                 345                 350

Pro Gly Ile Gly Val Pro Gly Ile Gly Val Pro Gly Ile Gly Val Pro
            355                 360                 365

Gly Ile Gly Val Pro Gly Ile Gly Val Pro Gly Ile Gly Val Pro Gly
        370                 375                 380

Ile Gly Val Pro Gly Ile Gly Val Pro Gly Ile Gly Val Pro Gly Ile
385                 390                 395                 400
```

-continued

```
Gly Val Pro Gly Ile Gly Val Pro Gly Ile Gly Val Pro Gly Ile Gly
                405                 410                 415
Val Pro Gly Ile Gly Val Pro Gly Ile Gly Val Pro Gly Ile Gly Val
            420                 425                 430
Pro Gly Ile Gly Val Pro Gly Ile Gly Val Pro Gly Ile Gly Val Pro
        435                 440                 445
Gly Ile Gly Val Pro Gly Ile Gly Val Pro Gly Ile Gly Val Pro Gly
    450                 455                 460
Ile Gly Val Pro Gly Ile Gly Val Pro Gly Ile Gly Val Pro Gly Ile
465                 470                 475                 480
Gly Val Pro Gly Ile Gly Val Pro Gly Ile Gly Val Pro Gly Ile Gly
                485                 490                 495
Val Pro Gly Ile Gly Val Pro Gly Ile Gly Val Pro Gly Ile Gly Val
            500                 505                 510
Pro Gly Ile Gly Val Pro Gly Ile Gly Val Pro Gly Ile Gly Val Pro
        515                 520                 525
Gly Ile Gly Val Pro Gly Ile Gly Val Pro Gly Ile Gly Val Pro Gly
    530                 535                 540
Ile Gly Val Pro Gly Ile Gly Val Pro Gly Ile Gly Val Pro Gly Val
545                 550                 555                 560
Gly Val Pro Gly Val Gly Val Pro Gly Glu Gly Val Pro Gly Val Gly
                565                 570                 575
Val Pro Gly Val Gly Val Pro Gly Val Gly Val Pro Gly Val Gly Val
            580                 585                 590
Pro Gly Glu Gly Val Pro Gly Val Gly Val Pro Gly Val Gly Val Pro
        595                 600                 605
Gly Val Gly Val Pro Gly Val Gly Val Pro Gly Glu Gly Val Pro Gly
    610                 615                 620
Val Gly Val Pro Gly Val Gly Val Pro Gly Val Gly Val Pro Gly Val
625                 630                 635                 640
Gly Val Pro Gly Glu Gly Val Pro Gly Val Gly Val Pro Gly Val Gly
                645                 650                 655
Val Pro Gly Val Gly Val Pro Gly Val Gly Val Pro Gly Glu Gly Val
            660                 665                 670
Pro Gly Val Gly Val Pro Gly Val Gly Val Pro Gly Val Gly Val Pro
        675                 680                 685
Gly Val Gly Val Pro Gly Glu Gly Val Pro Gly Val Gly Val Pro Gly
    690                 695                 700
Val Gly Val Pro Gly Val Gly Val Pro Gly Val Gly Val Pro Gly Glu
705                 710                 715                 720
Gly Val Pro Gly Val Gly Val Pro Gly Val Gly Val Pro Gly Val Gly
                725                 730                 735
Val Pro Gly Val Gly Val Pro Gly Glu Gly Val Pro Gly Val Gly Val
            740                 745                 750
Pro Gly Val Gly Val Pro Gly Val Gly Val Pro Gly Val Gly Val Pro
        755                 760                 765
Gly Glu Gly Val Pro Gly Val Gly Val Pro Gly Val Gly Val Pro Gly
    770                 775                 780
Val Gly Val Pro Gly Val Gly Val Pro Gly Glu Gly Val Pro Gly Val
785                 790                 795                 800
Gly Val Pro Gly Val Gly Val Pro Gly Ile Gly Val Pro Gly Ile Gly
                805                 810                 815
```

-continued

Val Pro Gly Ile Gly Val Pro Gly Ile Gly Val Pro Gly Ile Gly Val
                820                 825                 830

Pro Gly Ile Gly Val Pro Gly Ile Gly Val Pro Gly Ile Gly Val Pro
            835                 840                 845

Gly Ile Gly Val Pro Gly Ile Gly Val Pro Gly Ile Gly Val Pro Gly
        850                 855                 860

Ile Gly Val Pro Gly Ile Gly Val Pro Gly Ile Gly Val Pro Gly Ile
865                 870                 875                 880

Gly Val Pro Gly Ile Gly Val Pro Gly Ile Gly Val Pro Gly Ile Gly
                885                 890                 895

Val Pro Gly Ile Gly Val Pro Gly Ile Gly Val Pro Gly Ile Gly Val
                900                 905                 910

Pro Gly Ile Gly Val Pro Gly Ile Gly Val Pro Gly Ile Gly Val Pro
            915                 920                 925

Gly Ile Gly Val Pro Gly Ile Gly Val Pro Gly Ile Gly Val Pro Gly
        930                 935                 940

Ile Gly Val Pro Gly Ile Gly Val Pro Gly Ile Gly Val Pro Gly Ile
945                 950                 955                 960

Gly Val Pro Gly Ile Gly Val Pro Gly Ile Gly Val Pro Gly Ile Gly
                965                 970                 975

Val Pro Gly Ile Gly Val Pro Gly Ile Gly Val Pro Gly Ile Gly Val
                980                 985                 990

Pro Gly Ile Gly Val Pro Gly Ile  Gly Val Pro Gly Ile  Gly Val Pro
            995                  1000                  1005

Gly Ile  Gly Val Pro Gly Ile  Gly Val Pro Gly Ile  Gly Val Pro
        1010                  1015                  1020

Gly Ile  Gly Val Pro Gly Ile  Gly Val Pro Gly Ile  Gly Val Pro
        1025                  1030                  1035

Gly Ile  Gly Val Pro Gly Ile  Gly Val Pro Gly Ile  Gly Val Pro
        1040                  1045                  1050

Gly Ile  Gly Val Pro Gly Ile  Gly Val Pro Gly Ile  Gly Val Pro
        1055                  1060                  1065

Gly Ile  Gly Val Pro Gly Ile  Gly Val Pro Gly Ile  Gly Val Pro
        1070                  1075                  1080

Gly Ile  Gly Val Pro Gly Ile  Gly Val Pro Gly Ile  Gly Val Pro
        1085                  1090                  1095

Gly Ile  Gly Val Pro Gly Ile  Gly Val Pro Gly Ile  Gly Val Pro
        1100                  1105                  1110

Gly Ile  Gly Val Pro Gly Ile  Gly Val Pro Gly Ile  Gly Val Pro
        1115                  1120                  1125

Gly Ile  Gly Val Pro Gly Ile  Gly Val Pro Gly Ile  Gly Val Pro
        1130                  1135                  1140

Gly Ile  Gly Val Pro Gly Ile  Gly Val Pro Gly Ile  Gly Ala Val
        1145                  1150                  1155

Thr Gly Arg Gly Asp Ser Pro  Ala Ser Ser Val Pro  Gly Ile Gly
        1160                 1165                  1170

Val Pro Gly Ile Gly Val Pro  Gly Ile Gly Val Pro  Gly Ile Gly
        1175                 1180                  1185

Val Pro Gly Ile Gly Val Pro  Gly Ile Gly Val Pro  Gly Ile Gly
        1190                 1195                  1200

Val Pro Gly Ile Gly Val Pro  Gly Ile Gly Val Pro  Gly Ile Gly
        1205                 1210                  1215

-continued

```
Val Pro Gly Ile Gly Val Pro Gly Ile Gly Val Pro Gly Ile Gly
    1220            1225            1230

Val Pro Gly Ile Gly Val Pro Gly Ile Gly Val Pro Gly Ile Gly
    1235            1240            1245

Val Pro Gly Ile Gly Val Pro Gly Ile Gly Val Pro Gly Ile Gly
    1250            1255            1260

Val Pro Gly Ile Gly Ala Val Thr Gly Arg Gly Asp Ser Pro Ala
    1265            1270            1275

Ser Ser Val Pro Gly Ile Gly Val Pro Gly Ile Gly Val Pro Gly
    1280            1285            1290

Ile Gly Val Pro Gly Ile Gly Val Pro Gly Ile Gly Val Pro Gly
    1295            1300            1305

Ile Gly Val Pro Gly Ile Gly Val Pro Gly Ile Gly Val Pro Gly
    1310            1315            1320

Ile Gly Val Pro Gly Ile Gly Val
    1325            1330
```